US011891383B2

(12) United States Patent
Johnson et al.

(10) Patent No.: US 11,891,383 B2
(45) Date of Patent: Feb. 6, 2024

(54) CRYSTALLINE SALTS OF PEPTIDE EPOXYKETONE IMMUNOPROTEASOME INHIBITOR

(71) Applicant: KEZAR LIFE SCIENCES, South San Francisco, CA (US)

(72) Inventors: Henry Johnson, San Bruno, CA (US); Evan Lewis, Pacifica, CA (US); Sean Dalziel, Burlingame, CA (US); Dustin McMinn, Pacifica, CA (US)

(73) Assignee: KEZAR LIFE SCIENCES, South San Francisco, CA (US)

(*) Notice: Subject to any disclaimer, the term of this patent is extended or adjusted under 35 U.S.C. 154(b) by 0 days.

(21) Appl. No.: 17/953,935

(22) Filed: Sep. 27, 2022

(65) Prior Publication Data

US 2023/0106656 A1 Apr. 6, 2023

Related U.S. Application Data

(62) Division of application No. 17/066,556, filed on Oct. 9, 2020, now Pat. No. 11,479,548, which is a division of application No. 16/312,614, filed as application No. PCT/US2017/039961 on Jun. 29, 2017, now Pat. No. 10,836,756.

(60) Provisional application No. 62/356,287, filed on Jun. 29, 2016.

(51) Int. Cl.
C07D 413/12 (2006.01)
C07D 303/32 (2006.01)
A61P 29/00 (2006.01)
A61P 37/02 (2006.01)
A61P 1/04 (2006.01)
A61P 3/10 (2006.01)
A61P 5/14 (2006.01)
A61P 7/04 (2006.01)
A61P 7/06 (2006.01)
A61P 9/10 (2006.01)
A61P 11/06 (2006.01)
A61P 13/12 (2006.01)
A61P 17/00 (2006.01)
A61P 17/06 (2006.01)
A61P 19/02 (2006.01)
A61P 21/00 (2006.01)
A61P 21/04 (2006.01)
A61P 25/00 (2006.01)
A61P 31/04 (2006.01)
A61P 37/00 (2006.01)
A61P 37/06 (2006.01)
A61P 37/08 (2006.01)
A61P 43/00 (2006.01)

(52) U.S. Cl.
CPC ............ *C07D 413/12* (2013.01); *A61P 29/00* (2018.01); *A61P 37/02* (2018.01); *C07D 303/32* (2013.01); *C07B 2200/13* (2013.01)

(58) Field of Classification Search
CPC ..... C07D 413/12; C07D 303/32; A61P 29/00; A61P 37/02; A61P 1/04; A61P 3/10; A61P 5/14; A61P 7/04; A61P 7/06; A61P 9/10; A61P 11/06; A61P 13/12; A61P 17/00; A61P 17/06; A61P 19/02; A61P 21/00; A61P 21/04; A61P 25/00; A61P 31/04; A61P 31/336; A61P 37/00; A61P 37/06; A61P 37/08; A61P 43/00; C07B 2200/13

See application file for complete search history.

(56) References Cited

U.S. PATENT DOCUMENTS

| | | | |
|---|---|---|---|
| 4,522,811 A | 6/1985 | Eppstein et al. |
| 5,340,736 A | 8/1994 | Goldberg |
| 8,530,694 B2 | 9/2013 | Olhava et al. |
| 8,609,610 B2 | 12/2013 | Kisselev et al. |
| 8,609,654 B1 | 12/2013 | Shenk et al. |
| 8,697,646 B2 | 4/2014 | Phiasivongsa |
| 8,716,322 B2 | 5/2014 | Zhou et al. |
| 8,822,512 B2 | 9/2014 | Phiasivongsa et al. |
| 8,853,147 B2 | 10/2014 | Kirk et al. |
| 8,921,583 B2 | 12/2014 | Phiasivongsa et al. |
| 9,051,353 B2 | 6/2015 | Phiasivongsa et al. |
| 9,187,442 B2 | 11/2015 | Nishino et al. |
| 9,205,124 B2 | 12/2015 | Zhou et al. |
| 9,205,125 B2 | 12/2015 | Zhou et al. |
| 9,205,126 B2 | 12/2015 | Zhou et al. |
| 9,434,761 B2 | 9/2016 | Mcminn et al. |
| 2009/0203698 A1 | 8/2009 | Zhou et al. |
| 2011/0236428 A1 | 9/2011 | Kirk et al. |
| 2013/0150290 A1 | 6/2013 | Phiasivongsa et al. |

FOREIGN PATENT DOCUMENTS

| | | |
|---|---|---|
| CN | 101525370 A | 9/2009 |
| CN | 104710507 A | 6/2015 |
| EP | 1565193 A2 | 8/2005 |
| JP | 2016-515509 A | 5/2016 |
| WO | 98/10779 A1 | 3/1998 |

(Continued)

OTHER PUBLICATIONS

Bastin et al., Salt Selection and optimization procedures for pharmaceutical new chemical entities, Organic Process & Development, 4:427-35 (2000).

Berge et al., Pharmaceutical salts, Journal of pharmaceutical sciences, American chemical society and American pharmaceutical association, 66(1):1-19 (1977).

Brittain, Developing an appropriate salt form for an active pharmaceutical ingredient : American pharmaceutical review—The review of American pharmaceutical business & technology, American pharmaceutical Review, 12(7):62-65 (2009).

(Continued)

*Primary Examiner* — Sun Jae Yoo
(74) *Attorney, Agent, or Firm* — MARSHALL, GERSTEIN & BORUN LLP

(57) ABSTRACT

Provided herein is a peptide epoxyketone immunoproteasome inhibitor, crystal forms, salts, and processes for making the same, and formulations thereof.

18 Claims, 24 Drawing Sheets

(56) References Cited

FOREIGN PATENT DOCUMENTS

| WO | 2004/043374 A2 | 5/2004 |
|---|---|---|
| WO | 2012/151165 A1 | 11/2012 |
| WO | 2013/169897 A1 | 11/2013 |
| WO | 2014/056748 A1 | 4/2014 |
| WO | 2014/056954 A1 | 4/2014 |
| WO | 2014/152127 A1 | 9/2014 |
| WO | 2014/152134 A1 | 9/2014 |

OTHER PUBLICATIONS

Camille et al, Chapter 11 : Selected procedures for the preparation of pharmaceutically acceptable salts, Handbook or Pharmaceutical, 219-263 (2008).

Ciechanover et al., The Ubiquitin-Proteasome Proteolytic Pathway: Destruction for the Sake of Construction, Physiol Rev., 82:373-428, (2002).

Ciechanover, The ubiquitin-proteasome proteolytic pathway, Cell., 79:13-21 (1994).

Cohen, AIDS mood upbeat—for a change, Science, 267:959-960 (1995).

Collins, Endothelial nuclear factor-kappa B and the initiation of the atherosclerotic lesion, Lab. Invest., 68(5):499-508 (1993).

Dunetz et al., Large-Scale Applications of Amide Coupling Reagents for the Synthesis of Pharmaceuticals, Org. Process Res. Dev., 20:140-177 (2016).

Examiner initiated interview summary, U.S. Appl. No. 16/312,614, dated Dec. 11, 2019, 1 pages.

Flack et al., The use of X-ray crystallography to determine absolute configuration, Chirality, 20:681-690 (2008).

Garrett et al., Selective inhibitors of the osteoblast proteasome stimulate bone formation in vivo and in vitro, J clinical invest., 111:1771-1782 (2003).

Gonzalez et al., Proteasome function is required for encystation of entamoeba invadens, Arch med res 28 spec No. 139-140 (1997).

Han et al., Recent development of peptide coupling reagents in organic synthesis, Tetrahedron, 60:2447-2467 (2004).

Handbook for preparation of crystalline organic compounds—Principle and Knowhow, 57-79 (2008).

Hardy, The secret life of the hair follicle, Trends in genetics, 8:55-61 (1992).

Harris et al., Effects of transforming growth factor beta on bone nodule formation and expression of bone morphogenetic protein 2, osteocalcin, osteopontin, alkaline phosphatase, and type I collagen mRNA in long-term cultures of fetal rat calvarial osteoblasts, J. Bone Miner. Res., 9(6):855-863 (1994).

International Preliminary Report on Patentability for corresponding International Application No. PCT/US2017/039961, dated Jan. 10, 2019.

International Preliminary Report on Patentability for corresponding International Application No. PCT/US2017/039975, dated Jan. 10, 2019.

International Search Report and Written Opinion for corresponding International Application No. PCT/US2017/039961, dated Aug. 22, 2017.

International Search Report and Written Opinion for corresponding International Application No. PCT/US2017/039975, dated Oct. 23, 2017.

JP Office Action dated May 18, 2021 for JP Application No. 2018568267.

Kojima et al., Two-way cleavage of beta-amyloid protein precursor by multicatalytic proteinase, Fed. Eur. Biochem. Soc. 304:57-60 (1992).

Kumar et al., Effect of counterions on physicochemical properties of prazosin salts, AAPS pharmscitech 14(1):141-150 (2013).

Kumatori et al., Abnormally high expression of proteasomes in human leukemic cells, Proc. natl. acad. sci. USA 87:7071-7075 (1990).

Montalbetti et al., Amide bond formation and peptide coupling, Tetrahedron, 61:10827-10852 (2005).

Olovson et al., Oesophageal ulcerations and plasma levels of different alprenolol salts: Potential implications for the clinic, Acta pharmacol toxicol 58(1):55-60 (1986).

Palombella et al., The ubiquitin-proteasome pathway is required for processing the NF-kappa B1 precursor protein and the activation of NF-kappa B. Cell, 78(5): 773-85 (1994).

Paugam et al., Characterization and role of protozoan parasite proteasomes, Trends parasitol., 19:55-59 (2003).

Paulekuhn et al., Trends in active pharmaceutical ingredient salt selection based on analysis of the orange book database, J. Med. Chem., 50(26):6665-6672 (2007).

Pharmaceutical Salts, pp. 334-345, Retrieved from the Internet: URL:http://phoenix.tuwien.ac.at/pdf/pharmaceutical salts/Pharmaceutical_salts.pdf (1958).

Qureshi et al., The proteasome as a lipopolysaccharide-binding protein in macrophages: Differential effects of proteasome inhibition on lipopolysaccharide-induced signaling events, J. immunology, 171:1515-1525 (2003).

Requirement for Restriction/Election received for U.S. Appl. No. 16/312,688, dated Sep. 18, 2019, 8 pages.

Requirement for Restriction/Election, U.S. Appl. No. 16/312,614, dated Dec. 11, 2019, 9 pages.

Saal et al., Pharmaceutical salts: A summary on doses of salt formers from the orange book, European journal of pharmaceutical sciences, 49(4):614-623, (2013).

Shimada et al., Proteasome inhibitors improve the function of mutant lysosomal Alpha-glucosidase in fibroblasts from Pompe disease patient carrying c.546G>T mutation, Biochem. biophys. res. commun., 415(2):274-8 (2011).

Simsek et al., Hepatitis B virus large and middle glycoproteins are degraded by a proteasome pathway in glucosidase-inhibited cells but not in cells with functional glucosidase enzyme, J. virol., 79(20):12914-12920 (2005).

Stahly, The importance of selection of salts, and screening of polymorphism of crystals in pharmaceuticals, Pharm., 66(6):435-439 (2006).

Szalay et al., Ongoing coxsackievirus myocarditis is associated with increased formation and activity of myocardial immunoproteaseomes, Am. J. Pathol., 168(5):1542-1552 (2006).

Thanos et al., NF-kappaB: a lesson in family values, Cell, 80:529-532 (1995).

The Complete blog for the preparation of pharmaceutical salts, Retrieved from the Internet: URL:http://kilomentor.chemicalblogs.com/55kilomentor/archive/552 the complete blog for the preparation of pharmaceutical.salts.html, 1-10 (2008).

Traenckner et al., A proteasome inhibitor prevents activation of NF-kappaB and stabilizes a newly phosphorylated form of IkappaB-alpha that is still bound to NF-kappaB, Embo J., 13:5433-5441 (1994).

U.S. Appl. No. 17/066,556, Notice of Allowance, dated Jun. 21, 2022.

Wermuth, Newest Pharmaceutical Chemistry, vol. 2, Corp. TechnoMic, 347-365 (1999).

Yu et al., The ubiquitin-proteasome System facilitates the transfer of murine coronavirus from endosome to cytoplasm during virus entry, J. viral., 79(1):644-648 (2005).

CRYSTALLINE SALTS OF PEPTIDE EPOXYKETONE IMMUNOPROTEASOME INHIBITOR

BACKGROUND

Field of the Invention

The present disclosure relates to novel crystalline salts of (2S,3R)—N-[(2S)-3-(cyclopent-1-en-1-yl)-1-[(2R)-2-methyloxiran-2-yl]-1-oxopropan-2-yl]-3-hydroxy-3-(4-methoxyphenyl)-2-[(2S)-2-[2-(morpholin-4-yl)acetamido]propanamido]propanamide, or salt hydrates, pharmaceutical compositions thereof, methods for their preparation, and methods for their use.

Description of Related Technology

The compound, (2S,3R)—N-[(2S)-3-(cyclopent-1-en-1-yl)-1-[(2R)-2-methyloxiran-2-yl]-1-oxopropan-2-yl]-3-hydroxy-3-(4-methoxyphenyl)-2-[(2S)-2-[2-(morpholin-4-yl)acetamido]propanamido]propanamide ("compound G"), is useful as an immunoproteasome inhibitor:

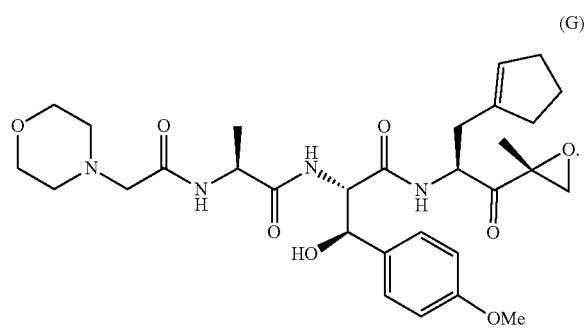 [SMILES: COc1ccc([C@@H](O)[C@H](NC(=O)[C@H](C)NC(=O)CN2CCOCC2)C(=O)N[C@@H](CC2=CCCC2)C(=O)[C@@]2(C)CO2)cc1]

(G)

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, a multi-catalytic protease, which cleaves proteins into short peptides through the action of its three major proteolytic activities. While having a general function in intracellular protein turnover, proteasome-mediated degradation also plays a key role in many processes such as major histocompatibility complex (MHC) class I antigen presentation, apoptosis, cell growth regulation, NF-κB activation, antigen processing, and transduction of pro-inflammatory signals.

PCT publication no. WO 2014/152134 describes tripeptide epoxyketone proteasome inhibitors and methods of using these compounds to treat diseases and conditions associated with aberrant immunoproteasome activity. Because tripeptide epoxyketone proteasome inhibitors, such as compound G, are useful in treating diseases and conditions in a patient, there is a need for highly soluble and stable forms of these compounds for their manufacturing, shipping, storage, and administration.

SUMMARY

In one aspect, the disclosure provides a crystalline salt having a structure:

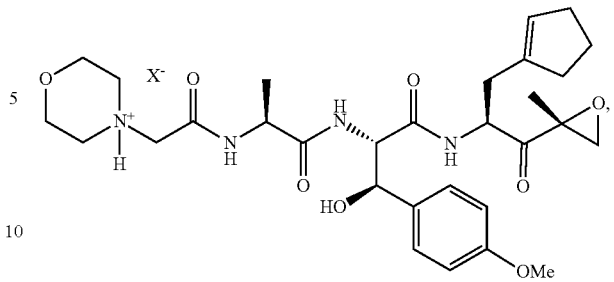

wherein X⁻ is a counterion. In some embodiments, X⁻ comprises maleate, fumarate, oxalate, malate, sulfate, methanesulfonate, 2-naphthalenesulfonate, phosphate, halide, tartrate, citrate, tosylate, propionate, and/or benzoate. In various cases, the salt is a salt hydrate.

In some cases, X⁻ comprises maleate. For example, the crystalline salt can be the monomaleate salt.

Form A. In some embodiments, the monomaleate crystalline salt exhibits Form A, characterized by (a) an X-ray powder diffraction ("XRPD") pattern comprising peaks at about 6.9, 17.3, and 17.8±0.2° 2θ using Cu Kα radiation, or (b) an XRPD pattern comprising peaks at about 6.9, 17.3, 17.8, 4.9, 6.8, 6.9, 7.7, 17.2, and 17.6±0.2° 2θ using Cu Kα radiation, or (c) an XRPD pattern comprising peaks at about 6.9, 17.3, 17.8, 4.9, 6.8, 6.9, 7.7, 17.2, 17.6, 10.9, 12.4, 13.5, 14.2, 16.1, 16.4, 18.5, 21.0, 22.0, 23.4, 23.7, 24.5, and 25.2±0.2° 2θ using Cu Kα radiation, or (d) XRPD pattern substantially as shown in FIG. 1, or (e) a differential scanning calorimetry ("DSC") thermogram substantially as shown in FIG. 2.

Form B. In some embodiments, the monomaleate crystalline salt exhibits Form B, characterized by (a) an XRPD pattern comprising peaks at about 7.2, 18.4, and 22.0±0.2° 2θ using Cu Kα radiation, or (b) an XRPD pattern comprising peaks at about 6.8, 7.2, 18.4, 6.6, 13.6, 22.0, 17.4, 14.5, 18.0, and 5.0±0.2° 2θ using Cu Kα radiation, or (c) an XRPD pattern substantially as shown in FIG. 13, or (d) a DSC thermogram substantially as shown in FIG. 17.

Form C. In some embodiments, the monomaleate crystalline salt exhibits Form C, characterized by (a) an XRPD pattern comprising peaks at about 7.4, 13.2, and 20.1±0.2° 2θ using Cu Kα radiation, or (b) an XRPD pattern comprising peaks at about 6.6, 13.2, 7.4, 20.1, 13.6, 6.9, 16.9, 3.7, 17.9, and 19.9±0.2° 2θ using Cu Kα radiation, or (c) an XRPD pattern substantially as shown in FIG. 7, or (d) a DSC thermogram substantially as shown in FIG. 8.

Form D. In some embodiments, the monomaleate crystalline salt exhibits Form D, characterized by (a) an XRPD pattern comprising peaks at about 4.9, 7.7 10.9, 12.4, 13.6, and 15.3±0.2° 2θ using Cu Kα radiation, or (b) an XRPD pattern comprising peaks at about 6.8, 4.9, 17.4, 15.3, 7.7, 3.4, 17.7, 13.6, 12.4, and 10.9±0.2° 2θ using Cu Kα radiation, or (c) an XRPD pattern substantially as shown in FIG. 9, or (d) a DSC thermogram substantially as shown in FIG. 10.

Form E. In some embodiments, the monomaleate crystalline salt exhibits Form E, characterized by (a) an XRPD pattern comprising peaks at about 6.4, 7.3, and 19.8±0.2° 2θ using Cu Kα radiation, or (b) an XRPD pattern comprising peaks at about 6.5, 3.3, 7.3, 19.8, 6.8, 16.5, 12.1, 21.5, 4.0, and 13.0±0.2° 2θ using Cu Kα radiation, or (c) an XRPD pattern substantially as shown in FIG. 11, or (d) a DSC thermogram substantially as shown in FIG. 12.

Form F. In some embodiments, the monomaleate crystalline salt exhibits Form F, characterized by (a) an XRPD pattern comprising peaks at about 6.3, 19.0, and 19.6±0.2° 2θ using Cu Kα radiation, or (b) an XRPD pattern comprising peaks at about 6.3, 7.1, 19.0, 17.5, 19.6, 17.9, 22.0, 13.5, 18.2, and 15.5±0.2° 2θ using Cu Kα radiation, or (c) an XRPD pattern substantially as shown in FIG. 19, or (d) a DSC thermogram substantially as shown in FIG. 20.

In some cases, X⁻ comprises fumarate. For example, the crystalline salt can be the monofumarate salt.

Form G. In some embodiments, the monofumarate crystalline salt exhibits Form G, characterized by (a) an XRPD pattern comprising peaks at about 6.4, 7.2, 13.8, 16.0, 17.4, 18.5, 18.7, 20.0, 20.9, 21.9, 24.5, and 25.8±0.2° 2θ using Cu Kα radiation, or (b) an XRPD pattern substantially as shown in FIG. 21, or (c) a DSC thermogram substantially as shown in FIG. 22. In some cases, the monofumarate salt comprises a monofumarate hydrate, and can be a mixture of hydrate and nonhydrate (or anhydrate).

In some embodiments, X⁻ comprises oxalate. In various embodiments, X⁻ comprises malate. In some cases, X⁻ comprises sulfate. In various cases, X⁻ comprises methanesulfonate. In some embodiments, X⁻ comprises 2-naphthalenesulfonate. In various embodiments, X⁻ comprises phosphate. In some cases, a halide (e.g., chloride, bromide, iodide). In various cases, X⁻ comprises tartrate. In some embodiments, X⁻ comprises citrate. In various embodiments, X⁻ comprises tosylate. In some cases, X⁻ comprises propionate. In various cases, X⁻ comprises benzoate. In any of these cases, the salt is present as a hydrate, or a mixture of hydrate and nonhydrate (or anhydrate).

In another aspect, the disclosure provides a method of preparing a crystalline salt disclosed herein by admixing:
(a) compound G:

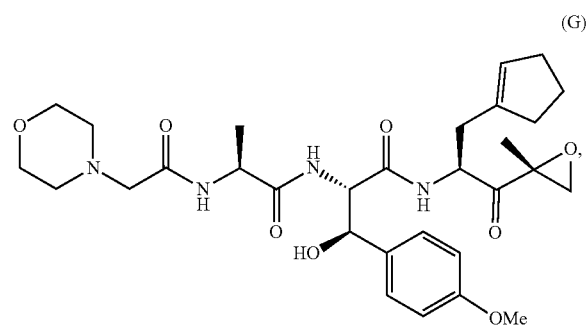 [SMILES: COc1ccc([C@@H](O)[C@H](NC(=O)[C@H](C)NC(=O)CN2CCOCC2)C(=O)N[C@@H](CC2=CCCC2)C(=O)[C@@]2(C)CO2)cc1]

(G)

(b) maleic acid, and
(c) a solvent
to form a suspension.

In some embodiments, the molar ratio of compound G to maleic acid is in a range of about 1:0.5 to 1:2 or about 1:1. In various cases, the solvent is selected from the group consisting of methanol ("MeOH"), ethanol ("EtOH"), isopropanol ("IPA"), ethyl acetate ("EtOAc"), isopropyl acetate ("IPAc"), tetrahydrofuran ("THF"), methyl tert-butyl ether ("MTBE"), acetone/n-heptane, acetone, diethyl ether ("Et₂O")/EtOAc, hexane/EtOAc, MTBE/EtOAc, toluene, 1,4-dioxane, acetonitrile ("ACN"), 1-butanol, aqueous mixtures of the foregoing, and combinations thereof. For example, the solvent can be EtOAc, IPAc, EtOH, aqueous mixtures thereof, or combinations thereof. In some embodiments, the admixing occurs at a temperature in a range of 0° C. to 80° C., or at a temperature in a range of 40° C. to 60° C. The admixing can occur for up to about 6 hours. In various embodiments, the method optionally includes cooling the suspension to 0° C. In some cases, the method optionally includes filtering the suspension to form a cake. In various cases, the method optionally includes washing, drying, or both washing and drying the cake. The method can further include recrystallizing the cake. Additionally or alternatively, the method can further include: (i) reforming compound G from the cake; and (ii) admixing the reformed compound G, maleic acid, and a solvent to form the crystalline salt.

The disclosure further provides a formulation comprising the crystalline salts disclosed herein and one or more excipients. In some embodiments, the formulation can be a liquid formulation. In some cases, the formulation can be a lyophilized formulation, wherein the lyophilized formulation can be reconstituted to a liquid form. In some cases, the crystalline salt is present in the liquid or reconstituted lyophilized formulation at a concentration in a range of about 1 mg/ml to about 150 mg/ml, or about 10 mg/ml to about 70 mg/ml, or about 30 mg/ml to about 50 mg/ml, based on the weight of the free base of crystalline salt.

In some embodiments, the one or more excipients in the formulation is selected from the group consisting of a surfactant, a tonicity agent, a buffer, and combinations thereof. In some cases, the lyophilized formulation can optionally include a cyroprotectant, a bulking agent, or both. In various embodiments, the surfactant is polysorbate, polyoxyl castor oil, poly(alkylene)glycol, caprylocaproyl polyoxylglyceride, polyoxyalkylene block copolymers, and combinations thereof. In various cases, the tonicity agent is a salt, a polyol, or combinations thereof. In some cases, the liquid formulation or the reconstituted lyophilized formulation is isotonic. In some embodiments, the buffer is selected from the group consisting of citrate, phosphate, histidine, succinate, acetate, maleate, gluconate, and combinations thereof. In various cases, the liquid formulation or the reconstituted lyophilized formulation exhibits a pH in a range of about 3.0 to about 8.0, or about 4.0 to about 6.5. In various embodiments, the liquid formulation or reconstituted lyophilized formulation is suitable for parenteral administration to a subject (e.g., a human). In some cases, the parenteral administration can be intravenous, intramuscular, intraperitoneal, or subcutaneous. For example, the parenteral administration can be subcutaneous. In some embodiments, the formulation exhibits a bioavailability of at least 55%, or at least 60%, or at least 65%.

Another aspect of the disclosure provides a method of inhibiting immunoproteasome of a cell comprising contacting a cell with a crystalline salt or formulation thereof disclosed herein. In some embodiments, the immunoproteasome LMP7 is inhibited. In some cases, the contacting is in vivo. In various embodiments, the contacting comprises administering to a subject suffering from disorder associated with aberrant immunoproteasome activity. In some embodiments, the disorder is an autoimmune disease or inflammation. In some cases, the disease is psoriasis, dermatitis, systemic scleroderma, sclerosis, Crohn's disease, ulcerative colitis; respiratory distress syndrome, meningitis; encephalitis; uveitis; colitis; glomerulonephritis; eczema, asthma, chronic inflammation; atherosclerosis; leukocyte adhesion deficiency; rheumatoid arthritis; systemic lupus erythematosus (SLE); diabetes mellitus; multiple sclerosis; Reynaud's syndrome; autoimmune thyroiditis; allergic encephalomyelitis; Sjogren's syndrome; juvenile onset diabetes; tuberculosis, sarcoidosis, polymyositis, granulomatosis, vasculitis; pernicious anemia (Addison's disease); a disease involving leukocyte diapedesis; central nervous system (CNS) inflammatory disorder; multiple organ injury syndrome; hemolytic anemia; myasthenia gravis; antigen-antibody complex mediated disease; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Beheet disease; giant cell arteritis; immune complex nephritis; IgA nephropathy; IgM polyneuropathies; immune thrombocytopenic purpura (ITP) or autoimmune thrombocytopenia. In various cases, the disorder is lupus, lupus nephritis, rheumatoid arthritis, diabetes, scleroderma, ankylosing spondylitis, psoriasis, multiple sclerosis, Hashimoto's disease, meningitis, or inflammatory bowel disease.

Further aspects and advantages will be apparent to those of ordinary skill in the art from a review of the following detailed description. While the methods disclosed herein are susceptible of embodiments in various forms, the description hereafter includes specific embodiments with the understanding that the disclosure is illustrative, and is not intended to limit the invention to the specific embodiments described herein.

DETAILED DESCRIPTION

Figure 1:
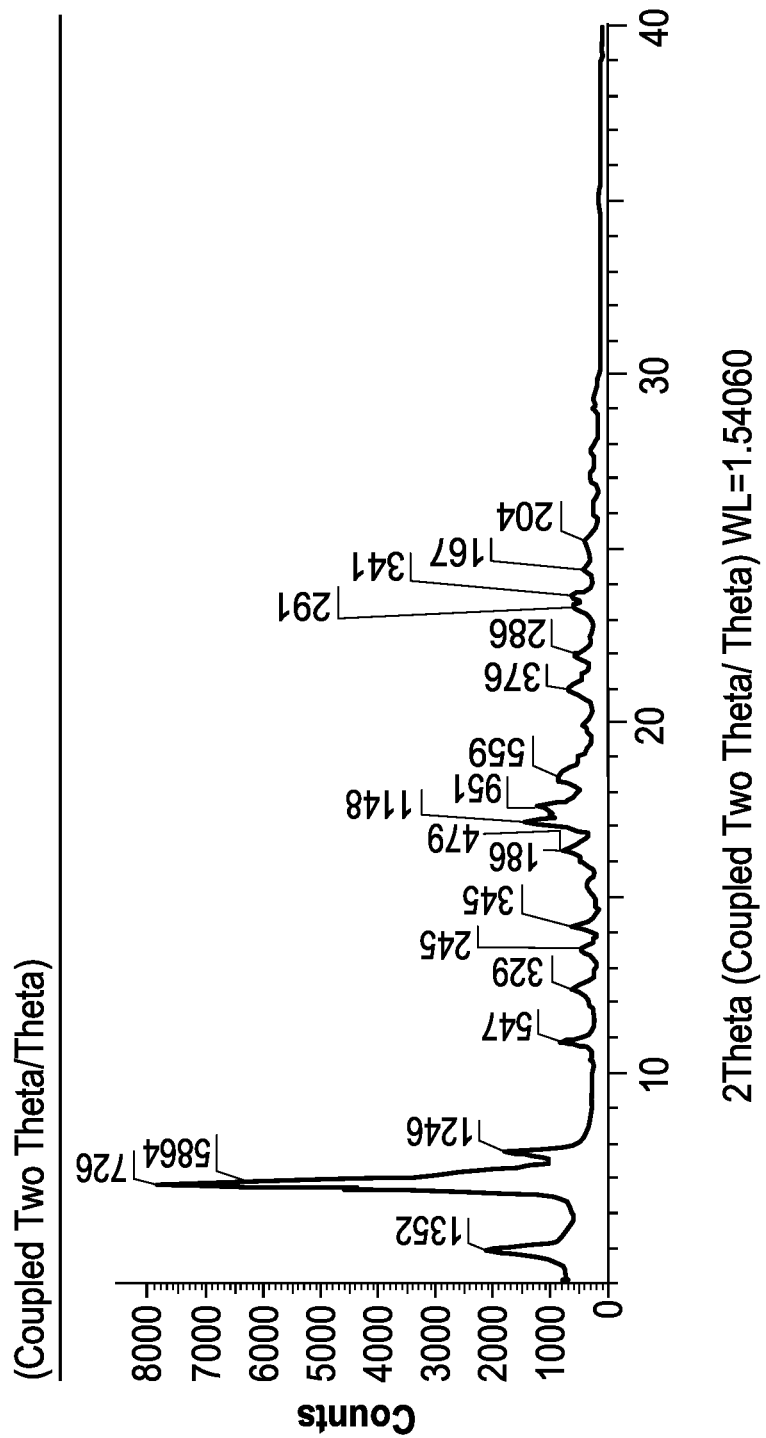
FIG. 1 depicts an X-ray powder diffraction (XRPD) pattern of Form A (monomaleate salt of compound G prepared in ethyl acetate).

Provided herein are novel, crystalline salt forms and hydrates thereof of (2S,3R)—N-[(2S)-3-(cyclopent-1-en-1-yl)-1-[(2R)-2-methyloxiran-2-yl]-1-oxopropan-2-yl]-3-hydroxy-3-(4-methoxyphenyl)-2-[(2S)-2-[2-(morpholin-4-yl)acetamido]propanamido]propanamide ("compound G"), useful as a proteasome inhibitor:

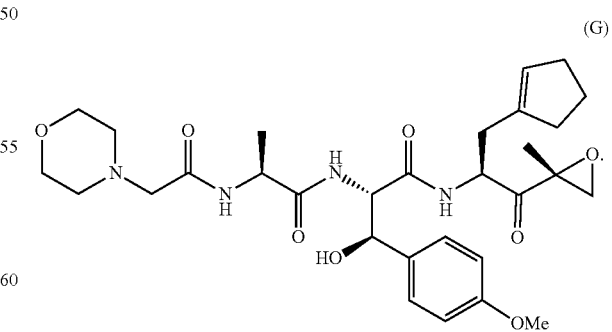

A crystalline salt form of compound G, as disclosed herein, is soluble and stable in solution, even at high concentrations. As such, a crystalline salt form of compound G is useful in pharmaceutical formulations suitable for, e.g., parenteral administration. Hydrates of salts of compound G also are useful for pharmaceutical formulations.

As used herein, the term "crystalline" refers to a solid in which the constituent atoms, molecules, or ions are arranged in a regularly ordered, repeating pattern in three dimensions.

As used herein, the term "hydrate" refers to a form of a substance that contains an association between the substance and water. The hydrate can be crystalline. As used herein, the term "monohydrate" refers a hydrate that contains one molecule of water per one molecule of the substrate.

The term "prophylactic or therapeutic" treatment is art-recognized and includes administration to the host of one or more of the subject compositions. If the subject composition is administered prior to clinical manifestation of the unwanted condition (e.g., disease or other unwanted state of the host animal) then the treatment is prophylactic, (i.e., it protects the host against developing the unwanted condition), whereas if the subject composition is administered after manifestation of the unwanted condition, the treatment is therapeutic, (i.e., it is intended to diminish, ameliorate, or stabilize the existing unwanted condition or side effects thereof).

A "therapeutically effective amount" of a compound with respect to the subject method of treatment, refers to an amount of the compound(s) in a preparation which, when administered as part of a desired dosage regimen (to a patient, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a patient's condition.

The compounds disclosed herein may be identified either by their chemical structure and/or chemical name herein. When the chemical structure and chemical name conflict, the chemical structure is determinative of the identity of the compound.

Unless otherwise indicated, terms and abbreviations used in this specification include the normal and customary meaning to those in the relevant field.

As the present disclosure's contribution is not limited to particular embodiments or aspects disclosed herein, the disclosure provides to one of ordinary skill in the art additional embodiments including changes and modifications to adapt to various usages and conditions. For example, changes and modifications to materials, methods of synthesis, or procedures described herein will be apparent to one of ordinary skill.

When ranges are used herein for physical properties, such as molecular weight, or chemical properties, such as chemical formulae, all combinations and subcombinations of ranges and specific embodiments therein are intended to be included.

Crystalline Salts and Hydrates Thereof of Compound G

In one aspect, the disclosure provides crystalline salts of compound G having a structure:

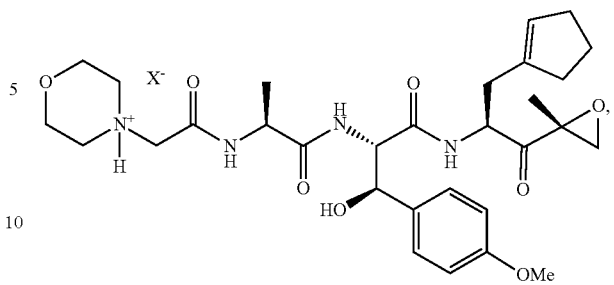

wherein $X^-$ is a counterion. Examples of $X^-$ include, for example

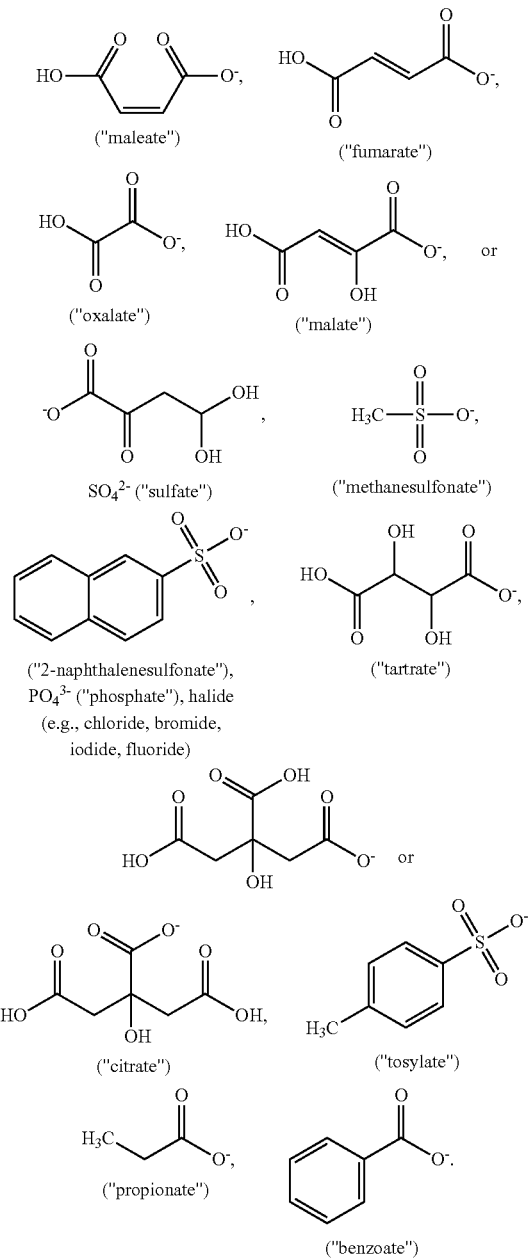

In some embodiments, X can be a dianion ($X^{2-}$). In these embodiments, a bridged salt can form with one molecule of $X^{2-}$ forming an ionic bond with each of two molecules of compound G:

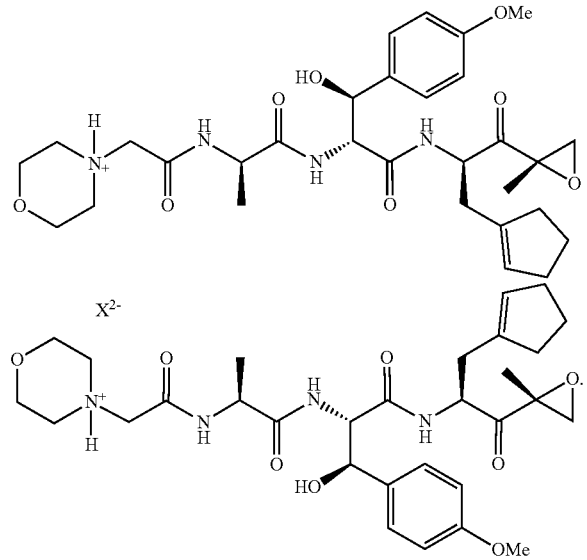

In another aspect the disclosure provides hydrates of compound G, such as monohydrates of compound G, or salt hydrates of compound G.

Monomaleate Salts and Hydrates of Compound G

In some embodiments, $X^-$ is maleate. In these embodiments, the crystalline salt of compound G can be the monomaleate salt (shown below). The monomaleate salt of compound G has a molecular weight of 586.7 g/mol, a p$K_a$ of 5, and appears as a white to yellow solid. The monomaleate salt of compound G exhibits a high aqueous solubility that exceeds 100 mg/ml. Such a high solubility is advantageous because it allows Form A to be used in parenteral pharmaceutical compositions at high concentrations.

The formation of the monomaleate salt was surprising because maleic acid has two acidic protons, each of which could form an ionic bond with a morpholino group on compound G to form a bridged maleate salt (shown below). However, the monomaleate salt forms over the bridged compound, regardless of whether a 0.5:1 molar ratio or a 1:1 molar ratio of maleic acid to compound G is used during its preparation. Therefore, the monomaleate salt can be reliably crystallized during manufacturing, regardless of the ratio of maleic acid starting material used, and despite the inhomogeneity of the reaction mixture that forms as maleic acid is added to compound G during its preparation.

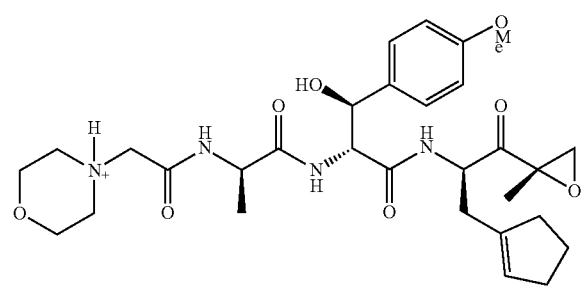

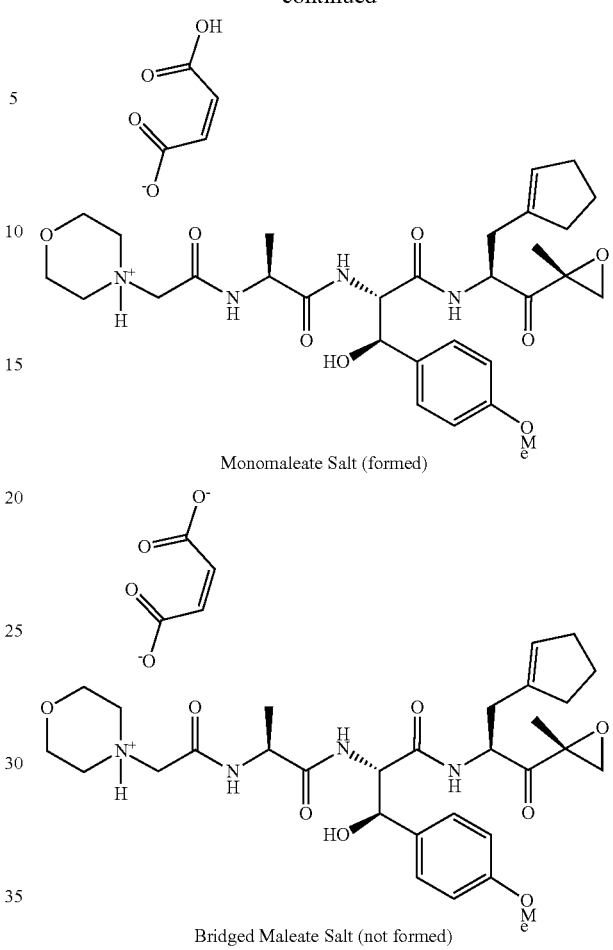

Monomaleate Salt (formed)

Bridged Maleate Salt (not formed)

The monomaleate salt of compound G (crystalline) is advantageous over compound G (amorphous) not only because of its crystallinity, but also because it has improved solubility in water. For example, the monomaleate salt of compound G exhibits a solubility in water exceeding 100 mg/ml at ambient temperature (e.g., 20° C. to 25° C.). In contrast, the solubility of compound G in water is only 8.9 mg/ml. See Table 1, below, for additional solubility data for compound G, and Table 2, below, for additional solubility data for the monomaleate salt of compound G.

TABLE 1

Solubility of Compound G (Amorphous)

| Solvent | pH | Solubility (mg/ml) | Solvent | pH | Solubility (mg/ml) |
|---|---|---|---|---|---|
| Water | 7.4 | 8.9 | PG, 100% | | >100 |
| 0.9% saline | 7.6 | 9.4 | PG, 67% | | >100 |
| PBS | 7.2 | 7.6 | PG, 33% | | 20.5 |
| 25 mM Na Citrate | 4.9 | 46.0 | PG, 10% | | 12.1 |
| 25 mM Na Citrate | 5.1 | 32.0 | PEG 400, 100% | | >50 |
| 25 mM Na Citrate | 5.2 | 24.8 | PEG 400, 67% | | >50 |
| 25 mM Na Citrate | 5.4 | 19.5 | PEG 400, 33% | | 17.4 |
| 25 mM Na Citrate | 5.8 | 11.2 | PEG 400, 10% | | 11.8 |
| 25 mM Na Citrate | 6.3 | 9.8 | glycerol, 100% | | not soluble |
| 25 mM Na Citrate | 6.8 | 8.8 | glycerol, 67% | | 5.4 |
| NMP, 100% | | >100 | glycerol, 33% | | 5.8 |
| NMP, 67% | | >100 | glycerol, 10% | | 8.6 |

TABLE 1-continued

Solubility of Compound G (Amorphous)

| Solvent | pH | Solubility (mg/ml) | Solvent | pH | Solubility (mg/ml) |
|---|---|---|---|---|---|
| NMP, 33% | | >100 | EtOH, 100% | | >100 |
| NMP, 10% | | 28.8 | EtOH, 67% | | >100 |
| EtOH, 33% | | 20.0 | | | |
| EtOH, 10% | | 13.7 | | | |

TABLE 2

Solubility Data for the Monomaleate Salt of Compound G (Crystalline)

| Solvent | Solubility (mg/ml) | Solvent | Solubility (mg/ml) |
|---|---|---|---|
| Acetonitrile ("ACN") | 1.30 | 2-Methyltetrahydrofuran ("THF") | 1.76 |
| Acetone | 3.19 | Methyl tert-butyl ether ("MTBE") | 0.17 |
| Dichloromethane ("DCM") | 0.21 | Isopropanol ("IPA") | 3.28 |
| Ethyl acetate ("EA") | 0.47 | Isopropyl acetate ("IPAc") | 0.13 |
| Ethanol ("EtOH") | 6.97 | Tetrahydrofuran ("THF") | 1.96 |
| Methanol ("MeOH") | 42.13 | Toluene | 0.02 |

The high aqueous solubility of the monomaleate salt of compound G in water is surprising because the crystalline salt is more thermodynamically stable than the amorphous form (compound G), and therefore, would be expected to be less soluble in water. Further, maleate salts of known compounds (e.g., alprenolol and prazosin) exhibited decreased solubility compared to other counterions, such as fumarate. See, e.g., Olovson et al., *Acta Pharmacol Toxicol* 58(1):55-60 (1986) and Kumar et al., *AAPS PHarmSciTech* 14(1): 141-150 (2013).

The monomaleate salt of compound G can be crystallized from, for example, ethyl acetate ("Form A'"), 95% ethanol or 3% water/acetone to form a monohydrate ("Form B"), acetone ("Form C"), acetonitrile ("Form D"), isopropyl alcohol ("Form E"), or MeOH/MTBE ("Form F"). Each of these forms can be characterized by the parameters described below. Each form can be characterized by X-ray powder diffraction ("XRPD"), differential scanning calorimerty ("DSC"), or thermogravimetric analysis ("TGA"), each as described in the Methods section, below. The dehydration of the crystal forms that occurs in both DSC and TGA is a kinetic event that is influenced by experimental parameters.

Form A (crystallized from ethyl acetate). Form A can be characterized by an XRPD pattern, obtained as set forth in the Methods section, having peaks at about 6.9, 17.3, and 17.8±0.2° 2θ using Cu Kα radiation. Form A also can be characterized by an XRPD pattern having peaks at about 4.9, 6.8, 6.9, 7.7, 17.2, and 17.6±0.2° 2θ using Cu Kα radiation. Form A optionally can be further characterized by an X-ray powder diffraction pattern having additional peaks at about 10.9, 12.4, 13.5, 14.2, 16.1, 16.4, 18.5, 21.0, 22.0, 23.4, 23.7, 24.5, and 25.2±0.2° 2θ using Cu Kα radiation. In some embodiments, Form A can be characterized by an X-ray powder diffraction pattern substantially as depicted in FIG. 1.

Figure 2:
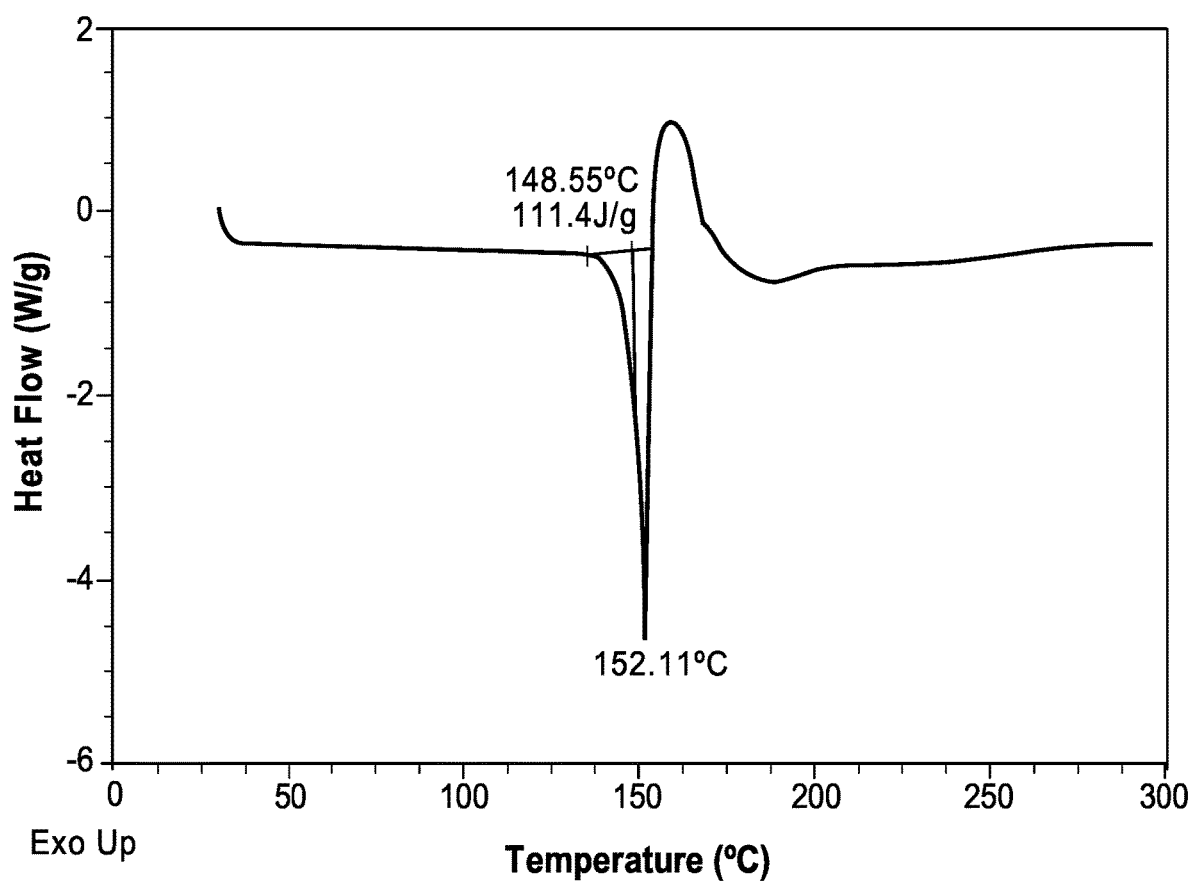
FIG. 2 depicts a differential scanning calorimetry (DSC) thermograph of Form A (monomaleate salt of compound G prepared in ethyl acetate).

Additionally or alternatively, Form A can be characterized by DSC, obtained as set forth in the Methods section. Form A can be characterized by a DSC thermograph having a dehydration endotherm with an onset in a range of about 135° C. to about 150° C. when Form A (crystallized from ethyl acetate) is heated in an aluminum pan. For example, in embodiments when Form A is heated from about 30° C. at a rate of about 10° C./min, Form A can be characterized by a DSC thermograph having a melting event with an onset of about 148° C. and a peak at about 152° C., as shown in FIG. 2 (crystallized from ethyl acetate). In some embodiments, Form A can be characterized by a DSC thermograph substantially as depicted in FIG. 2 (crystallized from ethyl acetate).

Figure 3:
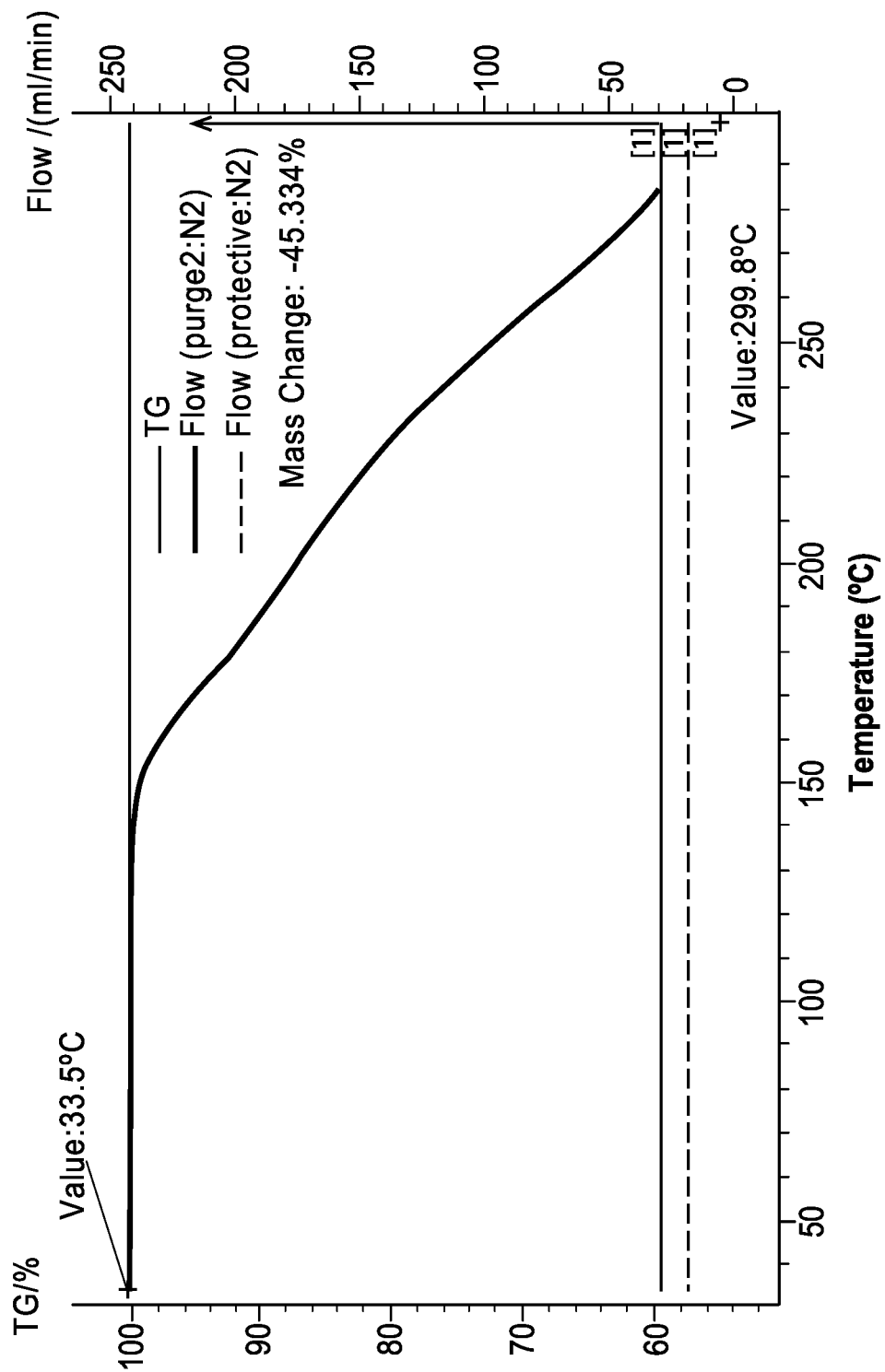
FIG. 3 depicts a thermogravimetric analysis ("TGA") trace of Form A (monomaleate salt of compound G prepared in ethyl acetate).

Additionally or alternatively, Form A can be characterized by TGA, obtained as set forth in the Methods section. Form A can be characterized by a weight loss in a range of about 1.5% to about 2.5%, with an onset temperature in a range of about 10° C. to about 30° C. For example, Form A (crystallized from ethyl acetate) can be characterized by a weight loss of about 0.8%, with an onset at about 34° C., as depicted in Figure. 3. In some embodiments, Form A (crystallized from ethyl acetate) can be characterized by a TGA trace substantially as depicted in Figure. 3.

Figure 4:
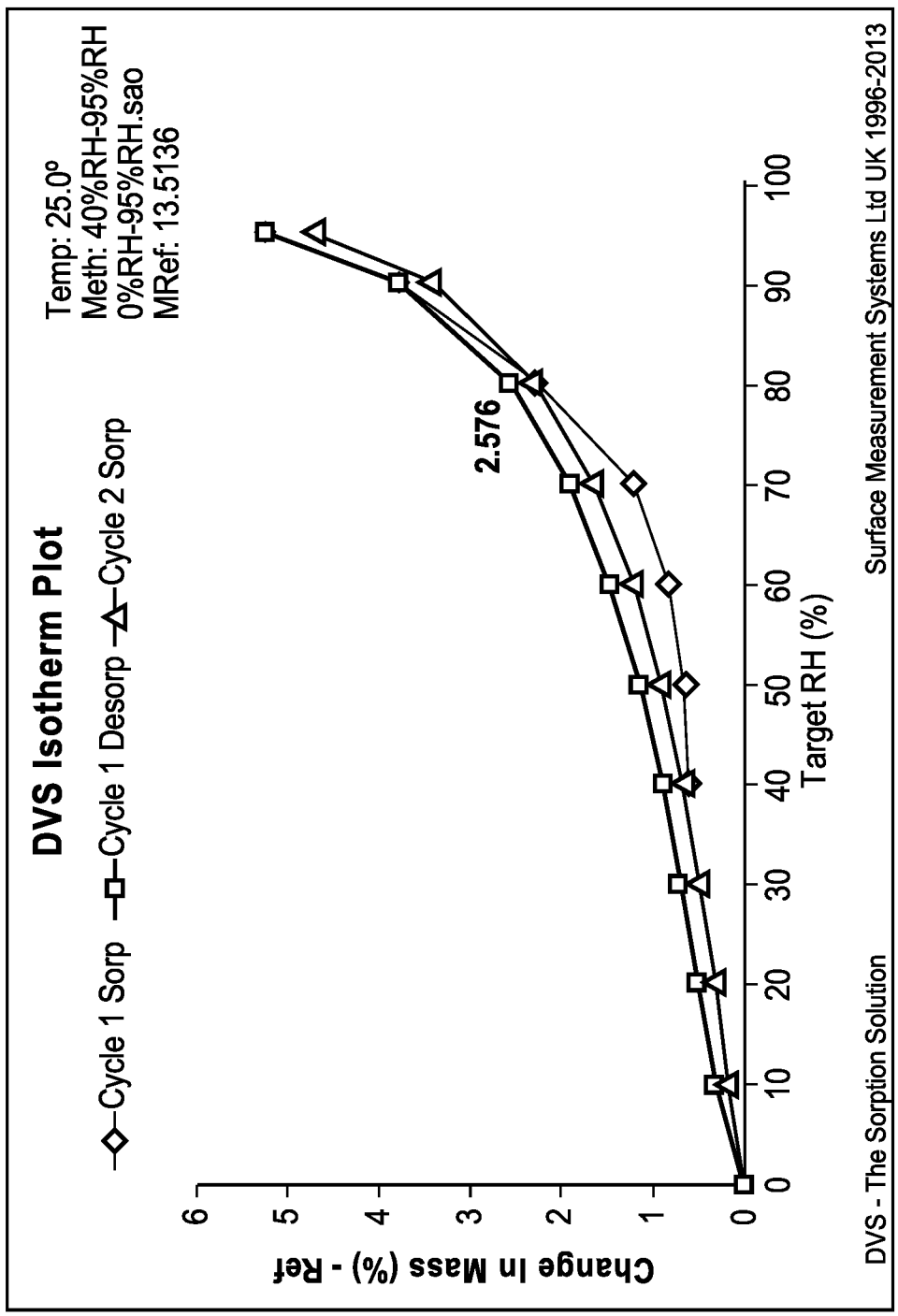
FIG. 4 depicts a DVS isotherm plot for Form A (40% relative humidity to 95% relative humidity).

Additionally or alternatively, Form A can be characterized by dynamic vapor sorption ("DVS"). For example, when subjected to DVS, as described in the Methods section, Form A demonstrated a total weight gain of about 3.5 wt. % between about 40% and about 95% relative humidity, as depicted in FIG. 4. Based on the uptake of approximately one mole of water per mole of Form A across the humidity range, the reversibility of this upon dehydration, the low extent of hysteresis, and the existence of a dehydration endotherm in FIG. 6 at temperature ranges below the melting event, but not in FIG. 2, Form A is understood to readily interconvert between anhydrous and hydrate versions of Form A based on humidity conditions. The anhydrous state can be crystallized using a solvent with poor water miscibility (such as, for example, ethyl acetate). The hydrate version can be crystallized using solvent containing water (such as, for example, 95% ethanol/5% water or 3% acetone/water). Interconversion between forms can be achieved post crystallization via controlled humidity exposure.

Figure 5:
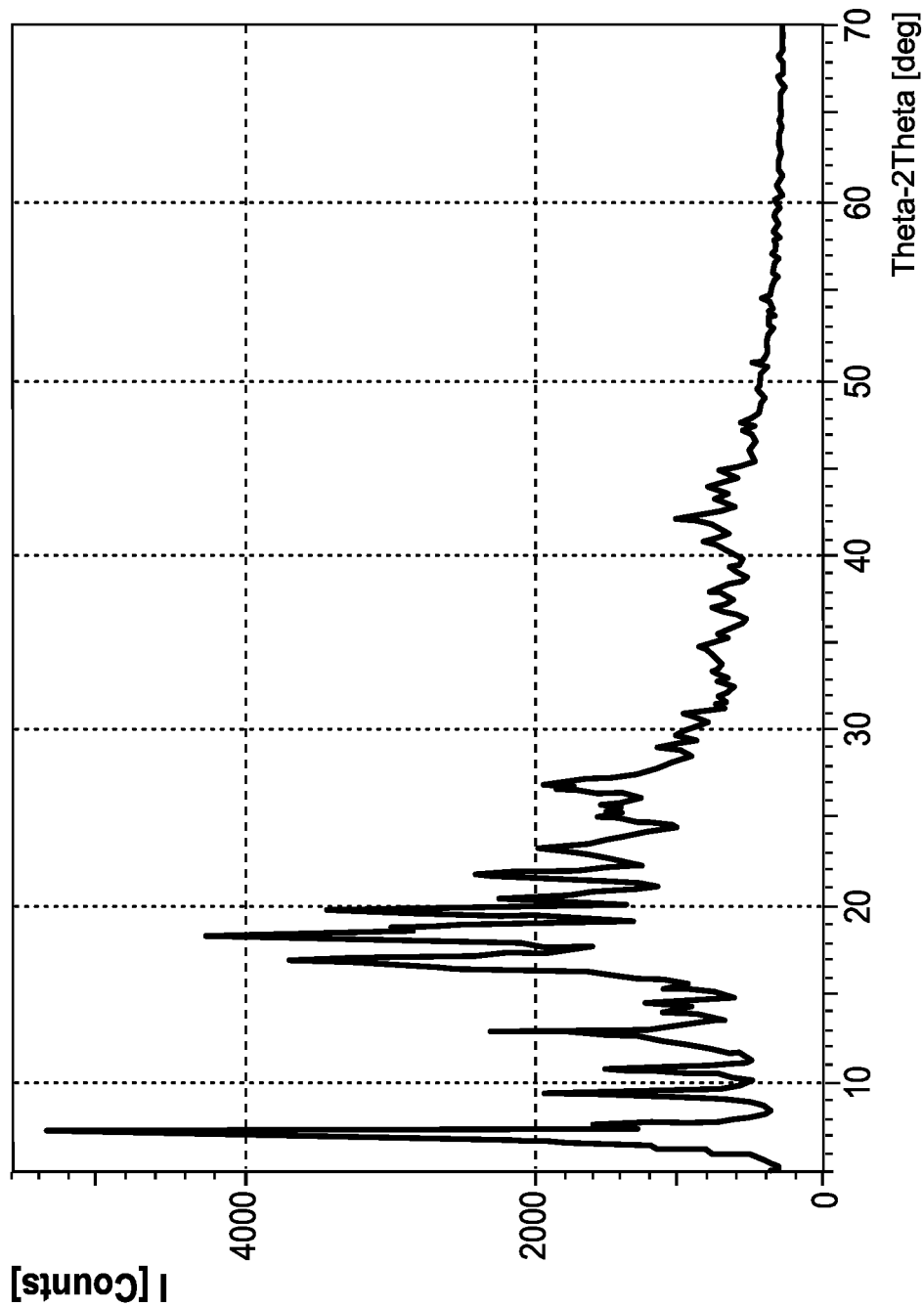
FIG. 5 depicts an XRPD pattern of Form B (monomaleate hydrate of compound G prepared in 95% ethanol).
Figure 6:
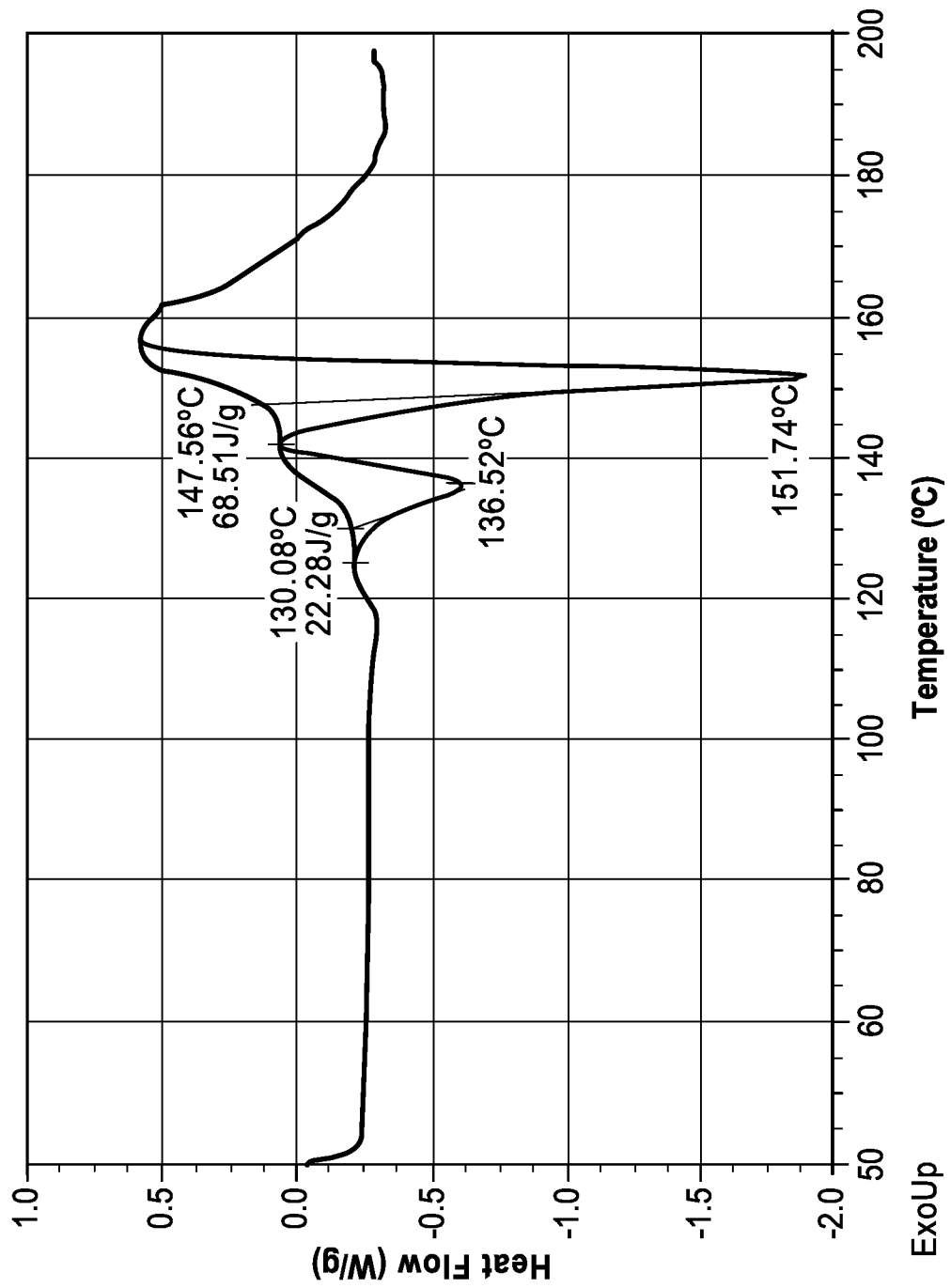
FIG. 6 depicts a DSC thermograph of Form B (monomaleate hydrate of compound G prepared in 95% ethanol).
Figure 13:
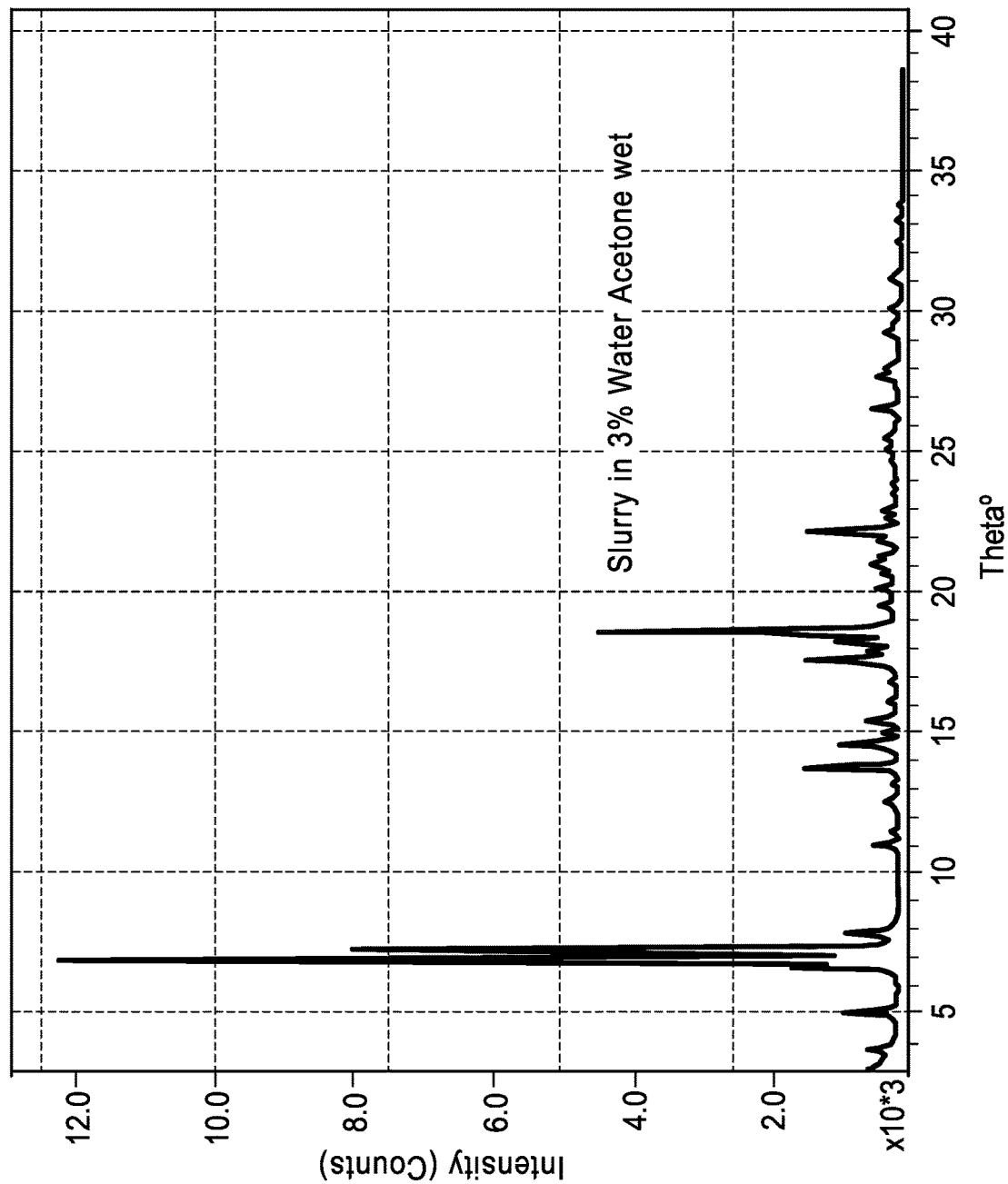
FIG. 13 depicts an XRPD pattern of Form B (monomaleate hydrate of compound G prepared in 3% water/acetone).
Figure 14:
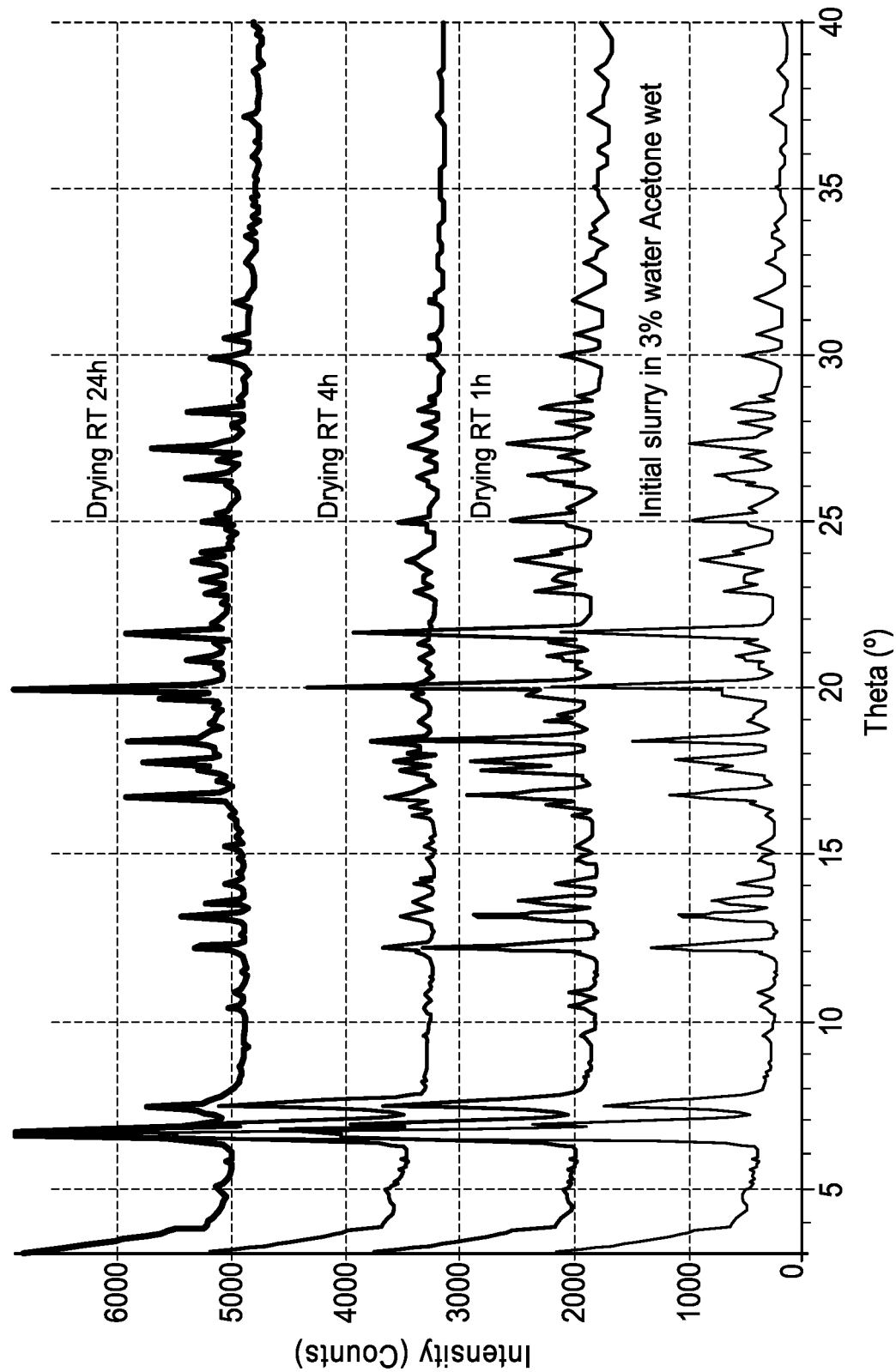
FIG. 14 depicts the XRPD patterns of Form B (monomaleate hydrate of compound G prepared in 3% water/acetone) under the indicated drying conditions.
Figure 15:
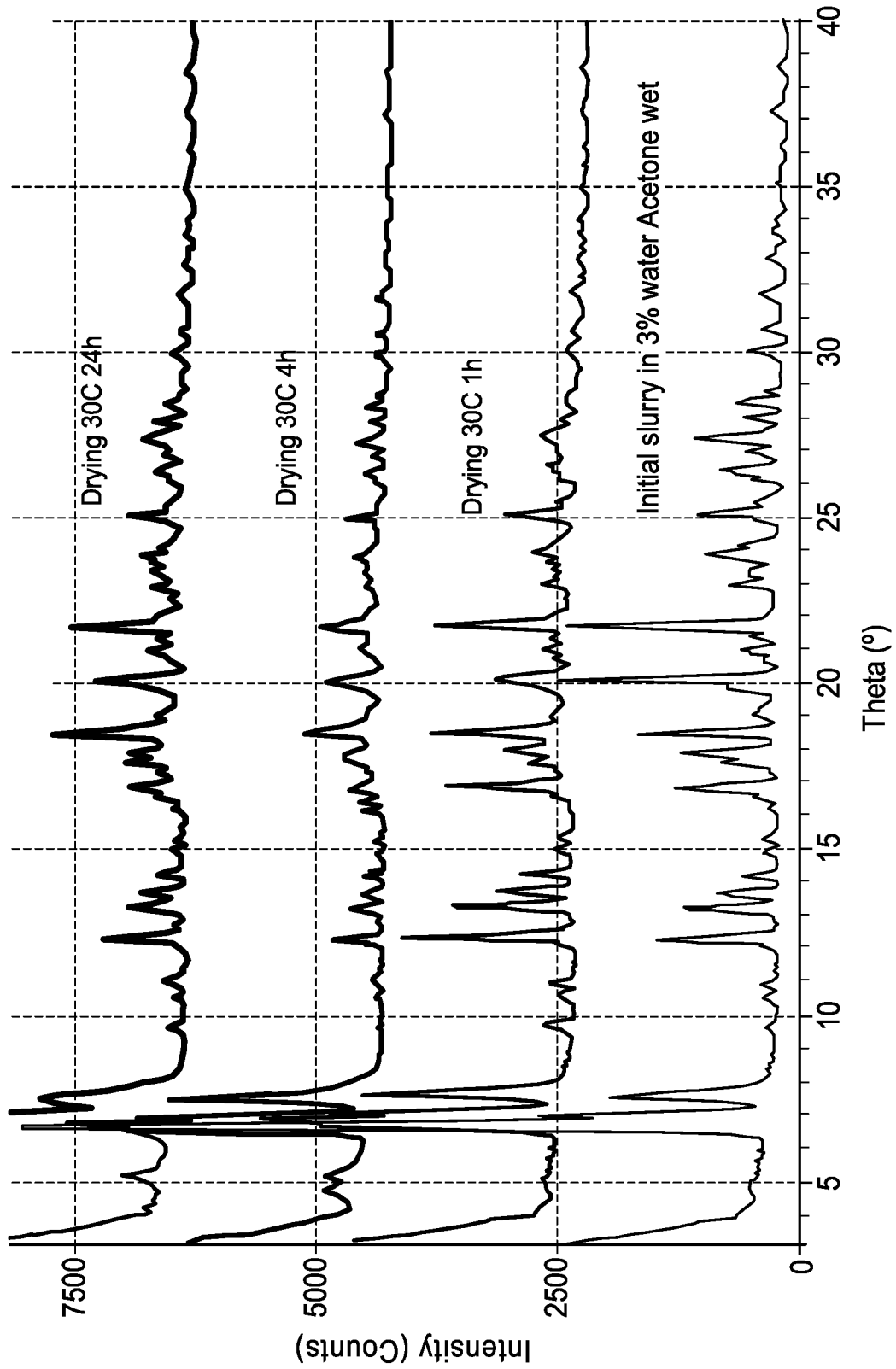
FIG. 15 depicts the XRPD patterns of Form B (monomaleate hydrate of compound G prepared in 3% water/acetone) under the indicated drying conditions.
Figure 16:
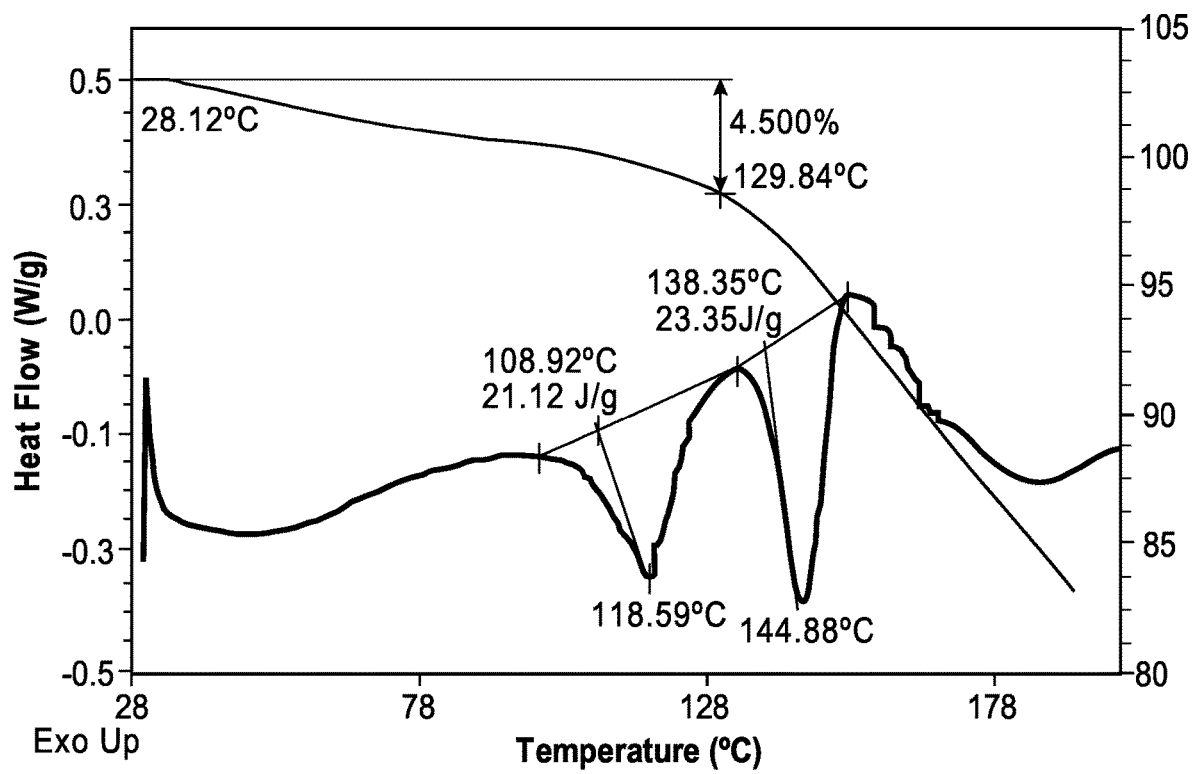
FIG. 16 depicts a TGA trace (top trace) and DSC thermograph (bottom trace) of Form B (monomaleate hydrate of compound G prepared in 3% water/acetone) after drying at room temperature overnight.
Figure 17:
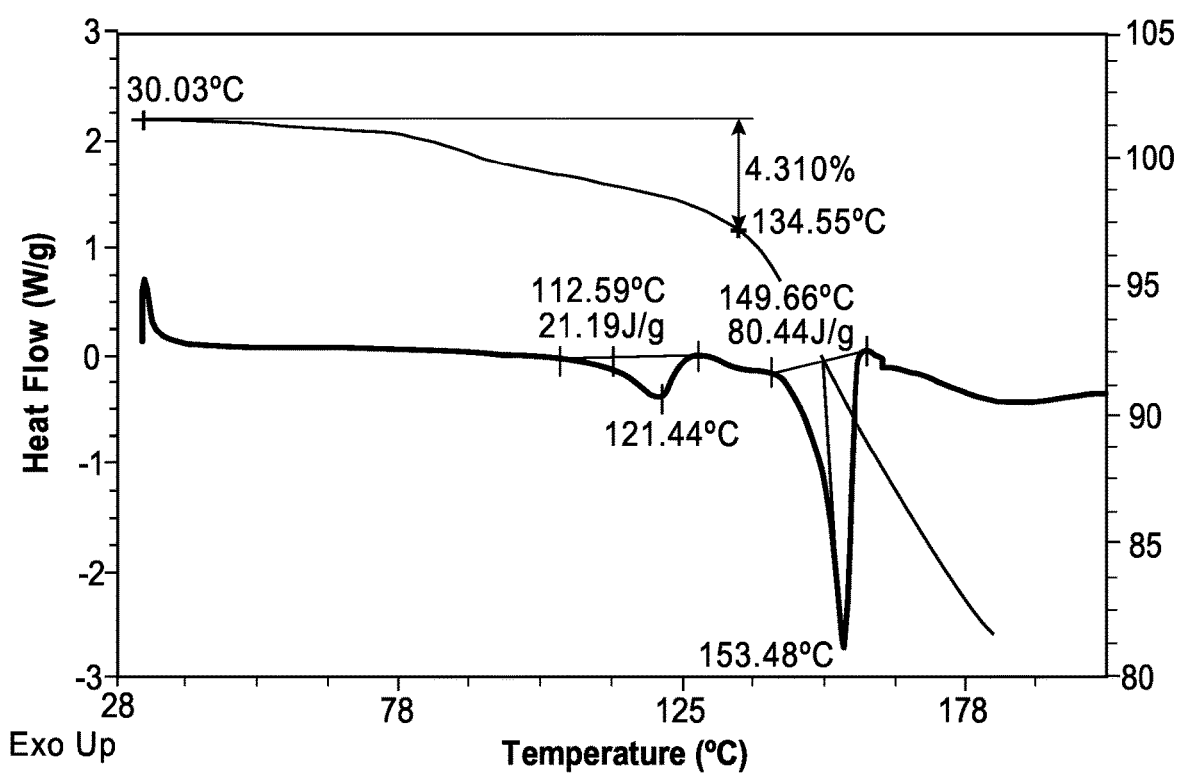
FIG. 17 depicts a TGA trace (top trace) and DSC thermograph (bottom trace) of Form B (monomaleate hydrate of compound G prepared in 3% water/acetone) after drying at 30° C. overnight.

Form B (monomaleate hydrate of compound G crystallized from 95% ethanol). In some embodiments, Form B (crystallized from 95% ethanol) can be characterized by an XRPD having peaks at about 6.1, 6.6, 7.2, 7.7, 9.4, 9.9, 10.8, 12.8, 14.5, 16.0, 16.4, 17.0, 17.4, 18.4, 18.8, 19.8, 20.6, 21.8, 23.4, 26.6, 27.0, and 42.0±0.2° 2θ using Cu Kα radiation. In some cases, Form B (crystallized from 95% ethanol) can be characterized by an X-ray powder diffraction pattern substantially as depicted in FIG. 5. Additionally or alternatively, Form B (crystallized from 95% ethanol) can be characterized by DSC, as set forth in the Methods section. For example, in embodiments when Form B (crystallized from 95% ethanol) is heated from about 30° C. at a rate of about 10° C./min, Form B (crystallized from 95% ethanol) can be characterized by a DSC thermograph having a melting event with an onset of about 148° C. and a peak at about 152° C., as shown in FIG. 6. In particular, Form B (crystallized from 95% ethanol) can be characterized by a DSC thermograph substantially as depicted in FIG. 6. Form B, the monomaleate hydrate of compound G, also can be crystallized from 3% water/acetone. In these embodiments, Form B can be characterized by an XRPD pattern, obtained as set forth in the Methods section, having peaks at about 7.2, 18.4, and 22.0±0.2° 2θ using Cu Kα radiation. Form B (crystallized from 3% water/acetone) also can be characterized by an XRPD pattern having peaks at about 6.8, 7.2, 18.4, 6.6, 13.6, 22.0, 17.4, 14.5, 18.0, and 5.0±0.2° 2θ using Cu Kα radiation. In some embodiments, Form B (crystallized from 3% water/acetone) can be characterized by an X-ray powder diffraction pattern substantially as depicted in FIG. 13. In some embodiments, Form B (crystallized from 3% water/acetone) can be subjected to further processing and dried to form a residue, as described in Example 9. As shown in FIGS. 14 and 15, the drying conditions did not affect the diffraction pattern. Additionally or alternatively, Form B (crystallized from 3% water/acetone) can be characterized by DSC, as set forth in the Methods section. For example, in embodiments when Form B (crystallized from 3% water/acetone) is heated from about 30° C. at a rate of about 10° C./min, Form B (crystallized from 3% water/acetone) can be characterized by DSC, TGA, and DVS, as described in Example 9, and depicted in FIGS. 16, 17, and 18, respectively. In some embodiments, Form B (crystallized from 3% water/acetone) can be characterized by a DSC thermograph substantially as depicted in FIG. 17. Additionally or alternatively, Form B (crystallized from 3% water/acetone) can be characterized by TGA, as described in the Methods section. In some embodiments, Form B (crystallized from 3% water/acetone) can be characterized by a TGA trace substantially as depicted in FIG. 17.

Figure 7:
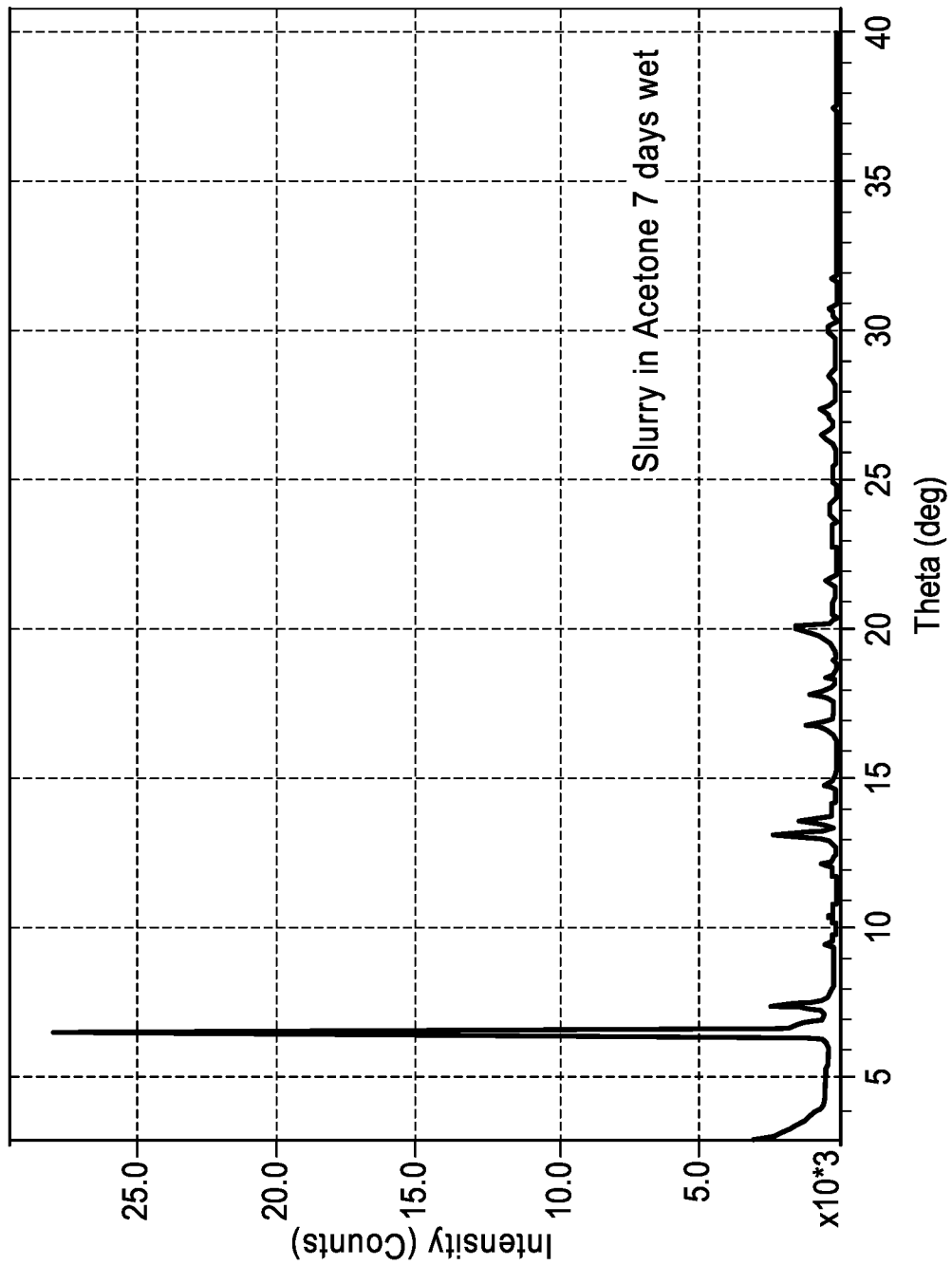
FIG. 7 depicts an XRPD pattern of Form C (monomaleate salt of compound G prepared in acetone).
Figure 8:
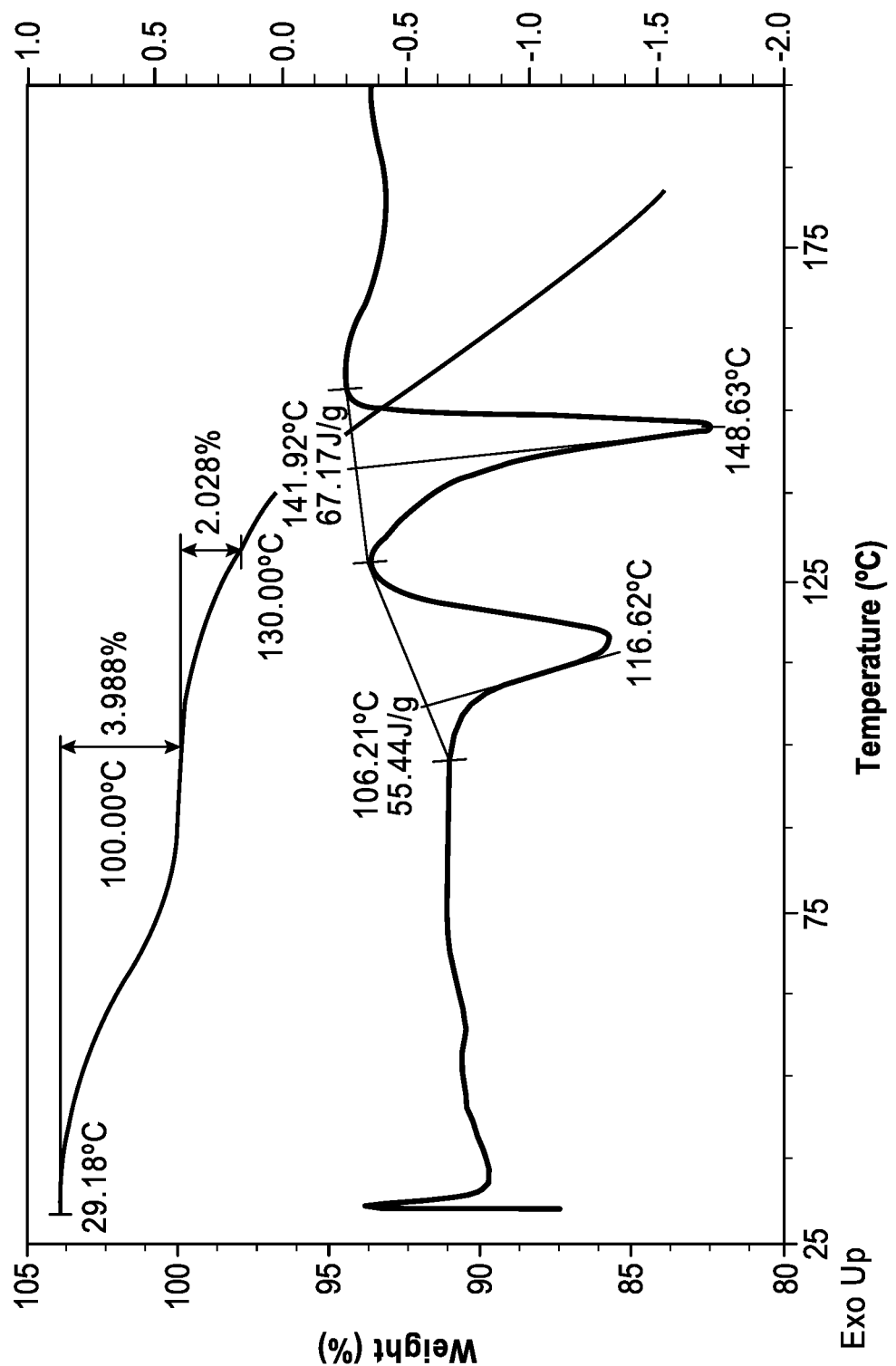
FIG. 8 depicts a TGA trace (top trace) and DSC thermograph (bottom trace) of Form C (monomaleate salt of compound G prepared in acetone).

Form C (crystallized from acetone). Form C can be characterized by an XRPD pattern, obtained as set forth in the Methods section, having peaks at about 7.4, 13.2, and 20.1 0.2° 2θ using Cu Kα radiation. Form C also can be characterized by an XRPD pattern having peaks at about 6.6, 13.2, 7.4, 20.1, 13.6, 6.9, 16.9, 3.7, 17.9, and 19.9±0.2° 2θ using Cu Kα radiation. In some embodiments, Form C can be characterized by an X-ray powder diffraction pattern substantially as depicted in FIG. 7. Additionally or alternatively, Form C can be characterized by DSC, as set forth in the Methods section. For example, in embodiments when Form C is heated from about 30° C. at a rate of about 10° C./min, Form C can be characterized by a DSC thermograph having a melting event with an onset of about 142° C. and a peak at about 159° C., as shown in FIG. 8. In particular, Form C can be characterized by a DSC thermograph substantially as depicted in FIG. 8. Additionally or alternatively, Form C can be characterized by TGA, as described in the Methods section. Thus, Form C can be characterized by a weight loss of about 6.0% from about 29° C. to 130° C., as depicted in Figure. 8. In some embodiments, Form C can be characterized by a TGA trace substantially as depicted in FIG. 8.

Figure 9:
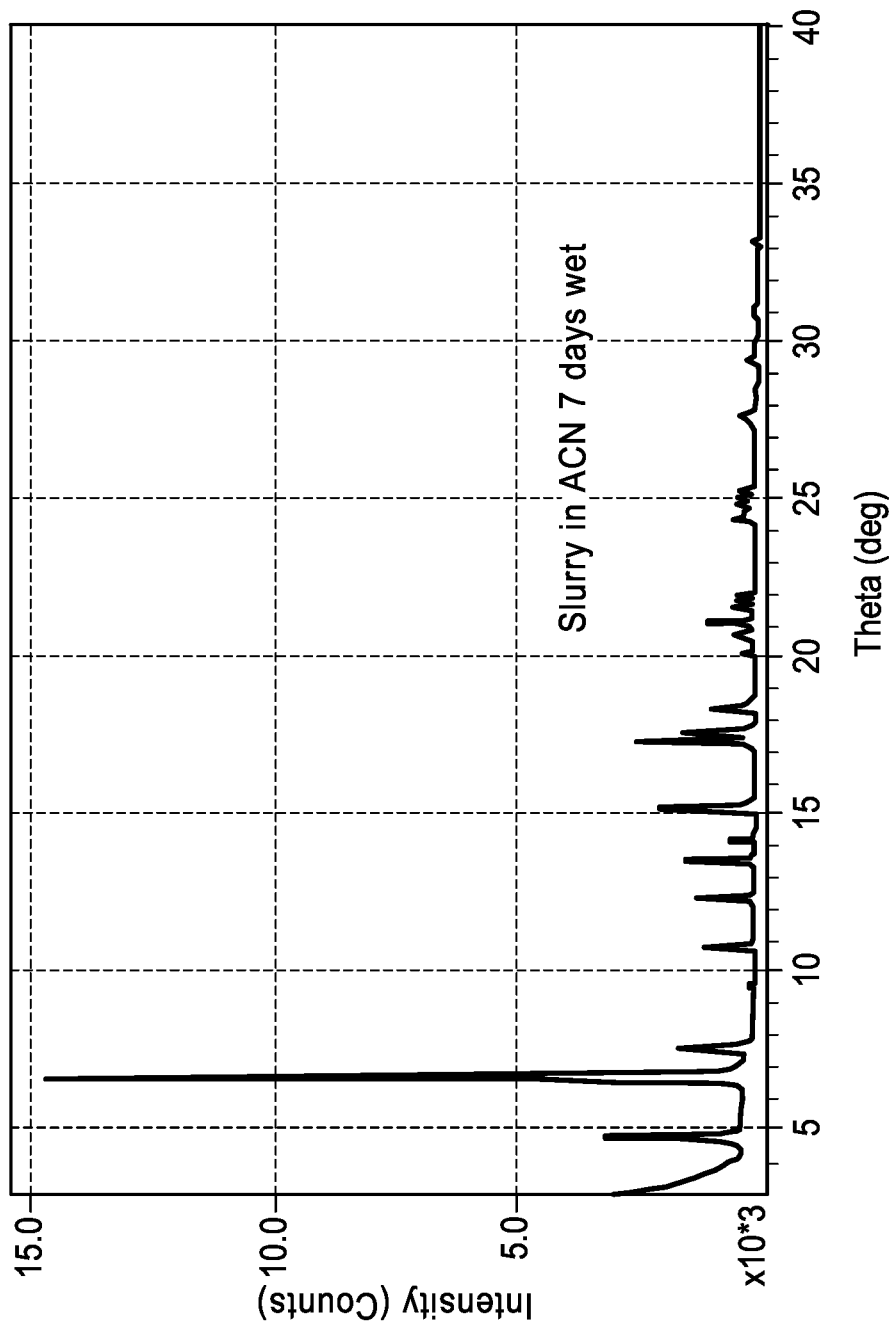
FIG. 9 depicts an XRPD pattern of Form D (monomaleate salt of compound G prepared in acetonitrile).
Figure 10:
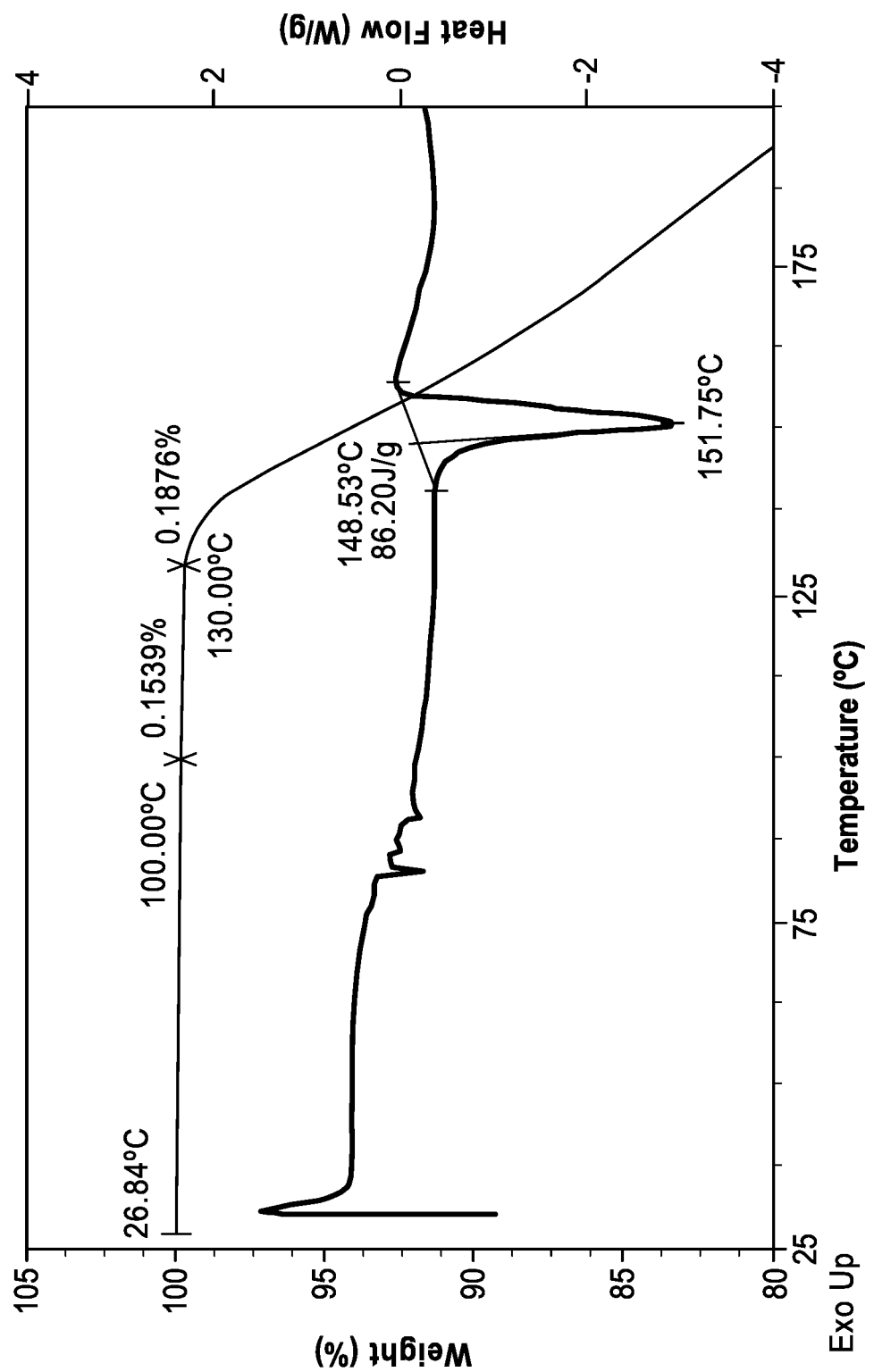
FIG. 10 depicts a TGA trace (top trace) and DSC thermograph (bottom trace) of Form D (monomaleate salt of compound G prepared in acetonitrile).

Form D (crystallized from acetonitrile). Form D can be characterized by an XRPD pattern, obtained as set forth in the Methods section, having peaks at about 4.9, 7.7 10.9, 12.4, 13.6, and 15.3±0.2° 2θ using Cu Kα radiation. Form D also can be characterized by an XRPD pattern having peaks at about 6.8, 4.9, 17.4, 15.3, 7.7, 3.4, 17.7, 13.6, 12.4, and 10.9±0.2° 2θ using Cu Kα radiation. In some embodiments, Form D can be characterized by an X-ray powder diffraction pattern substantially as depicted in FIG. 9. Additionally or alternatively, Form D can be characterized by DSC, as set forth in the Methods section. For example, in embodiments when Form D is heated from about 30° C. at a rate of about 10° C./min, Form D can be characterized by a DSC thermograph having a melting event with an onset of about 149° C. and a peak at about 152° C., as shown in FIG. 10. In particular, Form D can be characterized by a DSC thermograph substantially as depicted in FIG. 10. Additionally or alternatively, Form D can be characterized by TGA, as described in the Methods section. Thus, Form D can be characterized by a weight loss of about 0.3% from about 27° C. to 130° C., as depicted in Figure. 10. In some embodiments, Form D can be characterized by a TGA trace substantially as depicted in FIG. 10.

Figure 11:
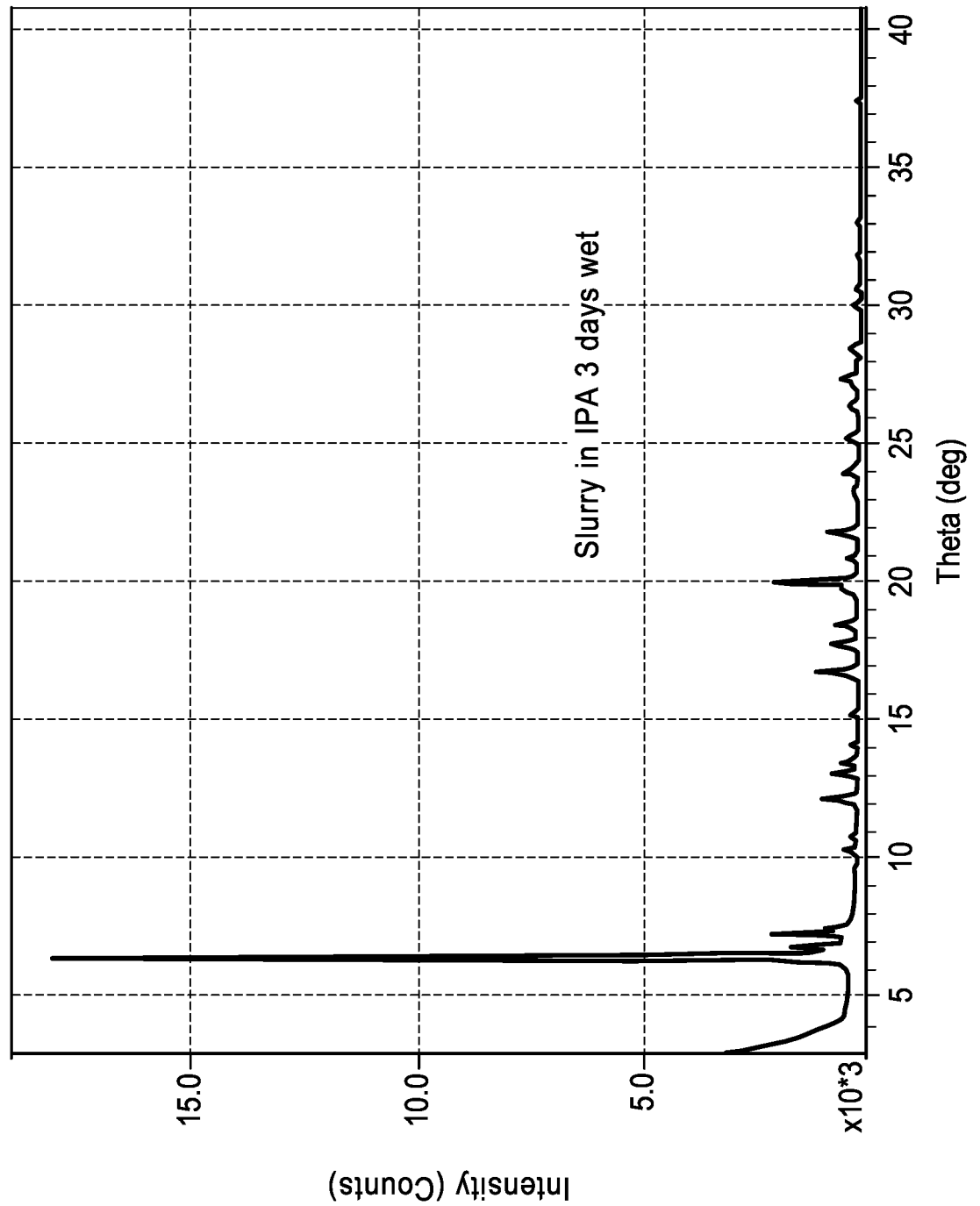
FIG. 11 depicts an XRPD pattern of Form E (monomaleate salt of compound G prepared in isopropyl alcohol).
Figure 12:
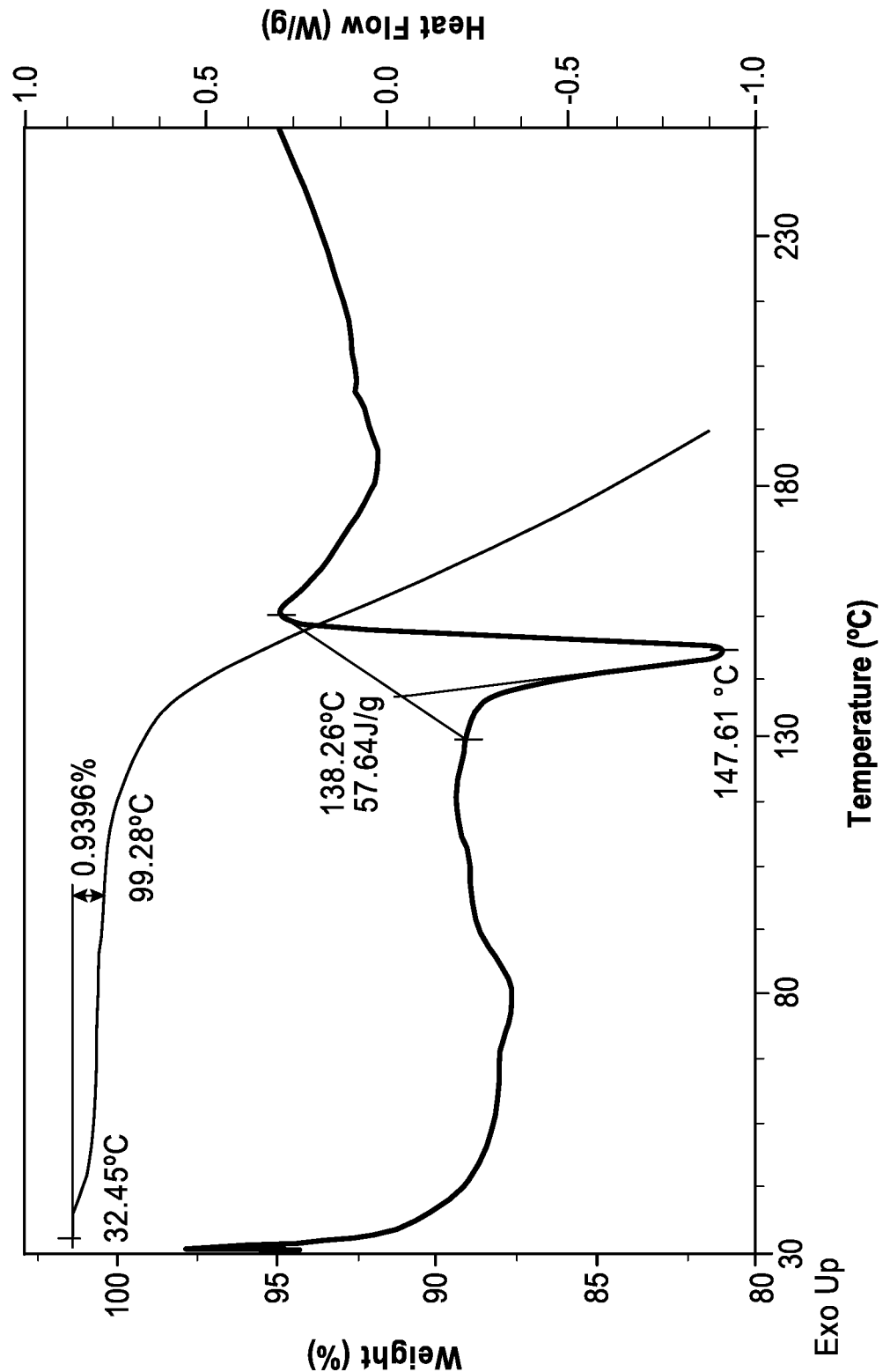
FIG. 12 depicts a TGA trace (top trace) and DSC thermograph (bottom trace) of Form E (monomaleate salt of compound G prepared in isopropyl alcohol).

Form E (crystallized from isopropyl alcohol). Form E can be characterized by an XRPD pattern, obtained as set forth in the Methods section, having peaks at about 6.4, 7.3, and 19.8±0.2° 2θ using Cu Kα radiation. Form E also can be characterized by an XRPD pattern having peaks at about 6.5, 3.3, 7.3, 19.8, 6.8, 16.5, 12.1, 21.5, 4.0, and 13.0±0.2° 2θ using Cu Kα radiation. In some embodiments, Form E can be characterized by an X-ray powder diffraction pattern substantially as depicted in FIG. 11. Additionally or alternatively, Form E can be characterized by DSC, as set forth in the Methods section. For example, in embodiments when Form E is heated from about 30° C. at a rate of about 10° C./min, Form E can be characterized by a DSC thermograph having a melting event with an onset of about 138° C. and a peak at about 148° C., as shown in FIG. 12. In particular, Form E can be characterized by a DSC thermograph substantially as depicted in FIG. 12. Additionally or alternatively, Form E can be characterized by TGA, as described in the Methods section. Thus, Form E can be characterized by a weight loss of about 0.9% from about 32° C. to 99° C., as depicted in FIG. 12. In some embodiments, Form E can be characterized by a TGA trace substantially as depicted in FIG. 12.

Figure 19:
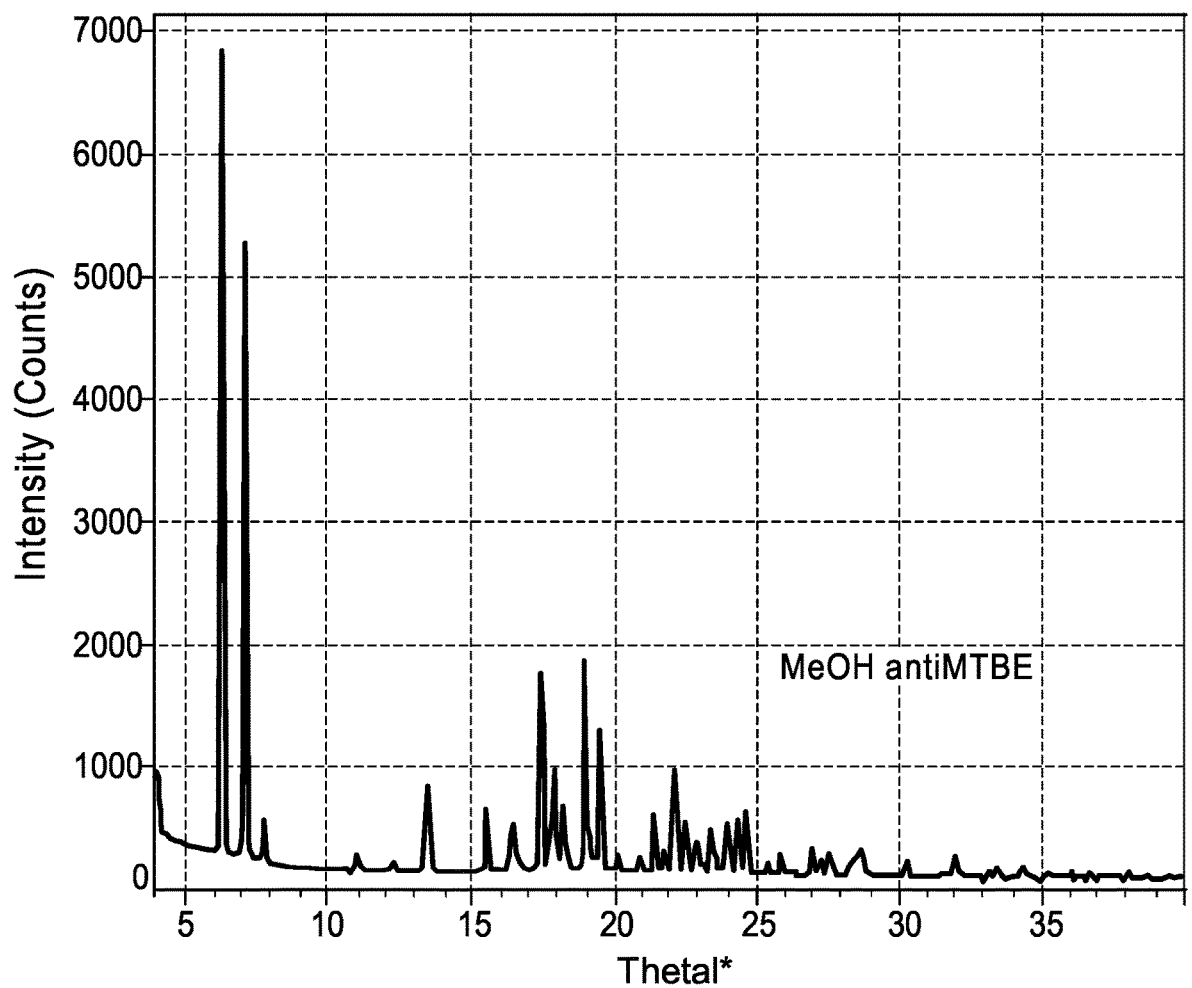
FIG. 19 depicts an XRPD pattern of Form F (monomaleate salt of compound G prepared in MeOH/MTBE).
Figure 20:
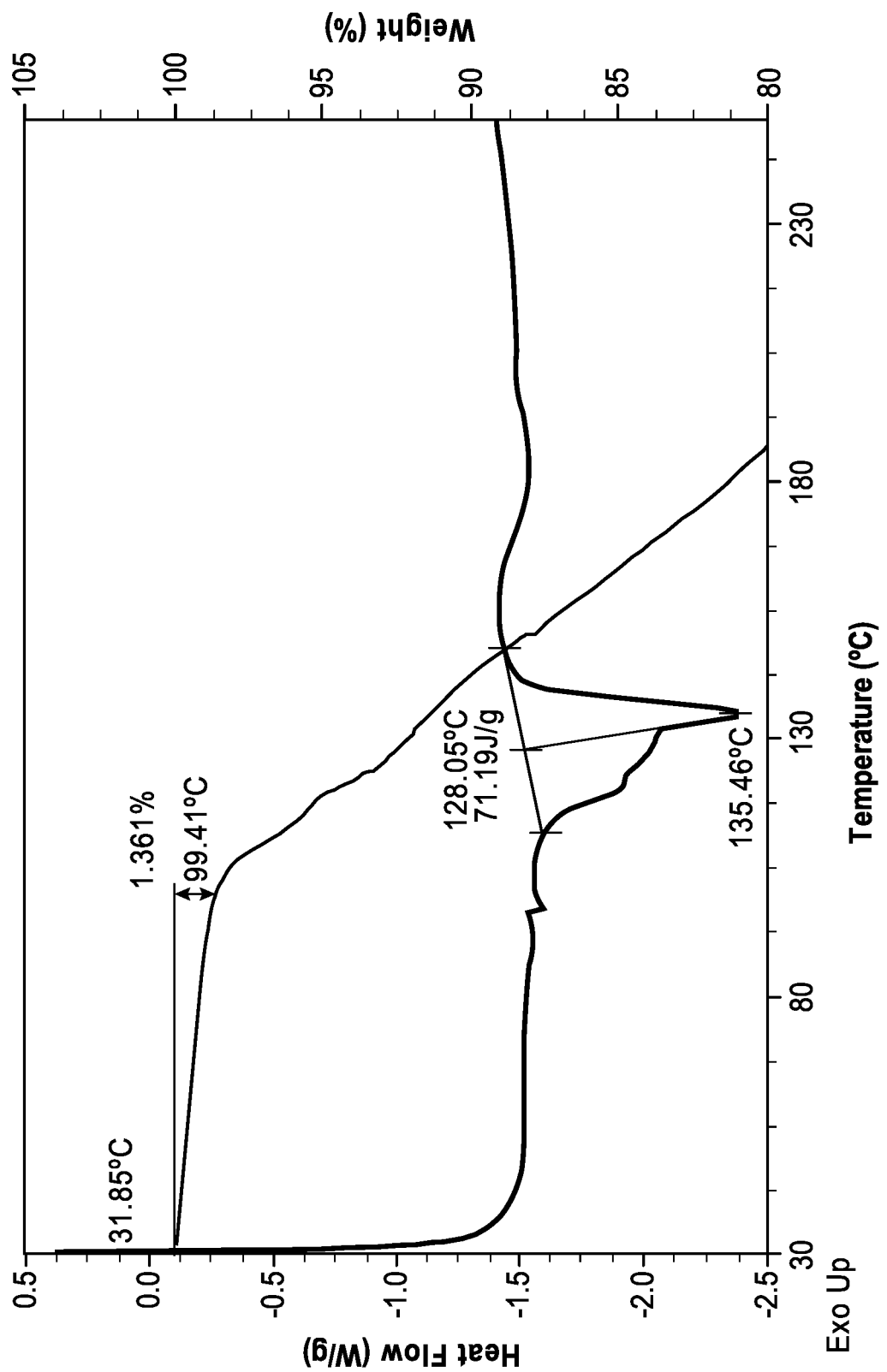
FIG. 20 depicts a TGA trace (top trace) and DSC thermograph (bottom trace) of Form F (monomaleate salt of compound G prepared in MeOH/MTBE).

Form F (crystallized from MeOH/MTBE). Form F can be characterized by an XRPD pattern, obtained as set forth in the Methods section, having peaks at about 6.3, 19.0, and 19.6 0.2° 2θ using Cu Kα radiation. Form F also can be characterized by an XRPD pattern having peaks at about 6.3, 7.1, 19.0, 17.5, 19.6, 17.9, 22.0, 13.5, 18.2, and 15.5±0.2° 2θ using Cu Kα radiation. In some embodiments, Form F can be characterized by an X-ray powder diffraction pattern substantially as depicted in FIG. 19. Additionally or alternatively, Form F can be characterized by DSC, as set forth in the Methods section. For example, in embodiments when Form F is heated from about 30° C. at a rate of about 10° C./min, Form F can be characterized by a DSC thermograph having a melting event with an onset of about 128° C. and a peak at about 135° C., as shown in FIG. 20. In particular, Form F can be characterized by a DSC thermograph substantially as depicted in FIG. 20. Additionally or alternatively, Form F can be characterized by TGA, as described in the Methods section. Thus, Form F can be characterized by a weight loss of about 1.4% from about 32° C. to 99° C., as depicted in FIG. 20. In some embodiments, Form F can be characterized by a TGA trace substantially as depicted in FIG. 20.

Monofumarate Salts of Compound G

In some embodiments, X⁻ is fumarate. In these embodiments, the crystalline salt of compound G can be the monofumarate salt (shown below). A specific crystalline form of the monofurmarate salt of compound G is Form G.

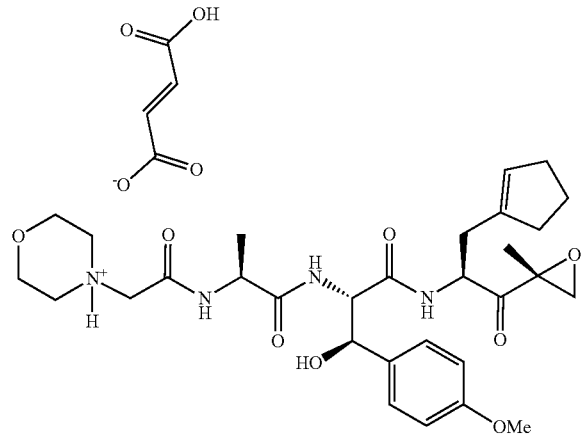

Monofumarate Salt

Form G can be characterized by one or more of the parameters described below.

Figure 21:
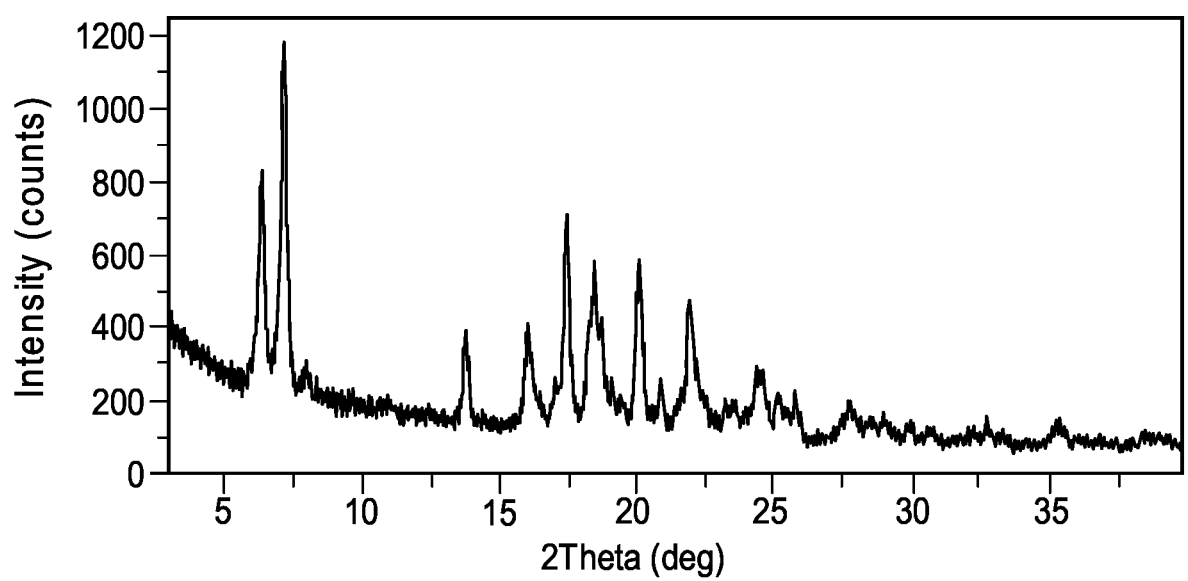
FIG. 21 depicts an XRPD pattern of Form G (monofumarate salt of compound G).

Form G can be characterized by an XRPD pattern, obtained as set forth in the Methods section, having peaks at about 6.4, 7.2, 13.8, 16.0, 17.4, 18.5, 18.7, 20.0, 20.9, 21.9, 24.5, and 25.8±0.2° 2θ using Cu Kα radiation. In embodiments, Form G can be characterized by an X-ray powder diffraction pattern substantially as depicted in FIG. 21.

Figure 22:
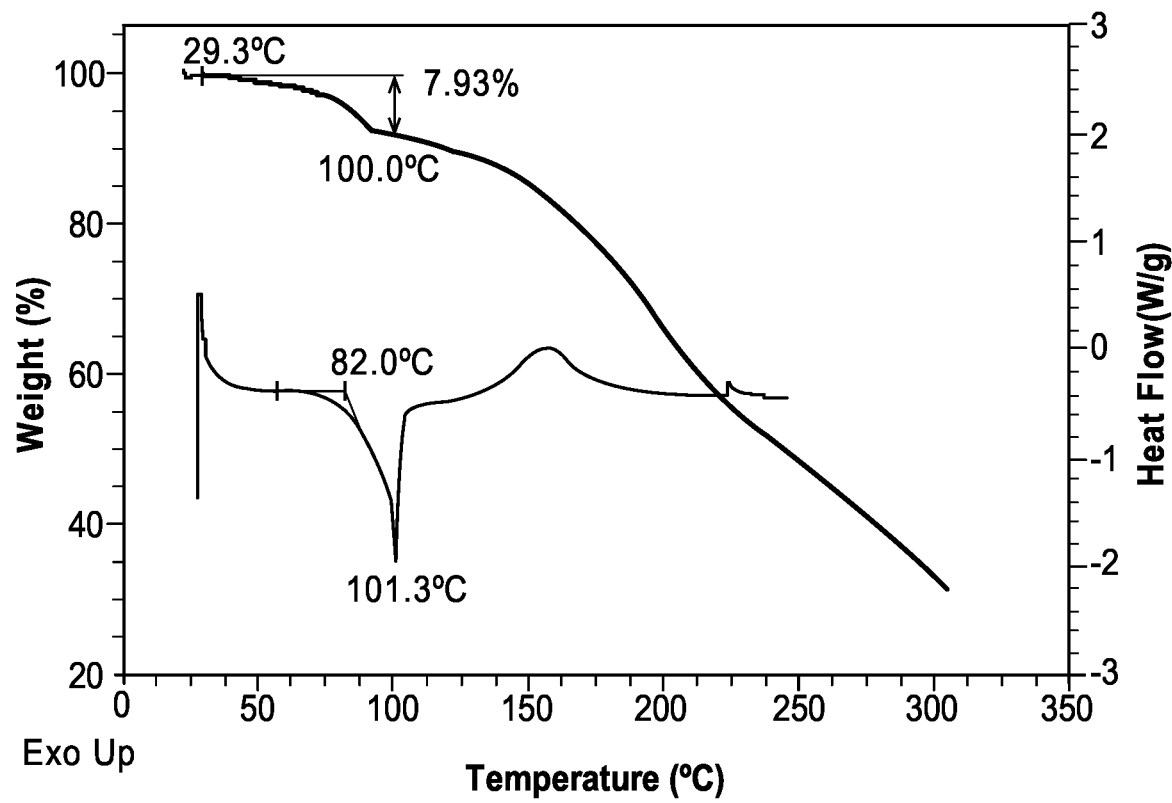
FIG. 22 depicts a TGA trace (top trace) and DSC thermograph (bottom trace) of Form G (monofumarate salt of compound G).

Additionally or alternatively, Form G can be characterized by DSC. DSC thermographs were obtained as set forth in the Methods section. The dehydration of Form G is a kinetic event that is influenced by experimental parameters. Thus, Form G can be characterized by a DSC thermograph having a dehydration endotherm with an onset in a range of about 75° C. to about 90° C. when Form G is heated in a crimped aluminum pan. For example, in embodiments when Form G is heated from about 25° C. at a rate of about 10° C./min, Form G can be characterized by a DSC thermograph having a dehydration endotherm with an onset of about 82° C. and a peak at about 101° C., as shown in FIG. 22. In some embodiments, Form G can be characterized by a DSC thermograph substantially as depicted in FIG. 22.

Oxalate Salts of Compound G

In some embodiments, $X^-$ is oxalate. In some cases, the crystalline salt of compound G can be the monooxalate salt. In various cases, oxalate reacts with the morpholino groups on two different compound G molecules to form a bridged salt. An oxalate salt of compound G can be characterized by one or more of the parameters described below in the Methods section (e.g., XRPD, DSC, TGA, and/or DVS).

Malate Salts of Compound G

In some embodiments, $X^-$ is malate. In some cases, the crystalline salt of compound G can be the monomalate salt. In various cases, malate reacts with the morpholino groups on two different compound G molecules to form a bridged salt. A malate salt of compound G can be characterized by one or more of the parameters described below in the Methods section (e.g., XRPD, DSC, TGA, and/or DVS).

Sulfate Salts of Compound G

In some embodiments, $X^-$ is sulfate. A sulfate salt of compound G can be characterized by one or more of the parameters described below in the Methods section (e.g., XRPD, DSC, TGA, and/or DVS).

Methanesulfonate Salts of Compound G

In some embodiments, $X^-$ is methanesulfonate. A methanesulfonate salt of compound G can be characterized by one or more of the parameters described below in the Methods section (e.g., XRPD, DSC, TGA, and/or DVS).

2-Naphthalenesulfonate Salts of Compound G

In some embodiments, $X^-$ is 2-naphthalenesulfonate. A 2-naphthalenesulfonate salt of compound G can be characterized by one or more of the parameters described below in the Methods section (e.g., XRPD, DSC, TGA, and/or DVS).

Phosphate Salts of Compound G

In some embodiments, $X^-$ is phosphate. A phosphate salt of compound G can be characterized by one or more of the parameters described below in the Methods section (e.g., XRPD, DSC, TGA, and/or DVS).

Halide Salts of Compound G

In some embodiments, $X^-$ is a halide (e.g., chloride, bromide, iodide, fluoride). A halide salt of compound G can be characterized by one or more of the parameters described below in the Methods section (e.g., XRPD, DSC, TGA, and/or DVS).

Tartrate Salts of Compound G

In some embodiments, $X^-$ is tartrate. A tartrate salt of compound G can be characterized by one or more of the parameters described below in the Methods section (e.g., XRPD, DSC, TGA, and/or DVS).

Citrate Salts of Compound G

In some embodiments, $X^-$ is citrate. A citrate salt of compound G can be characterized by one or more of the parameters described below in the Methods section (e.g., XRPD, DSC, TGA, and/or DVS).

Tosylate Salts of Compound G

In some embodiments, $X^-$ is tosylate. A tosylate salt of compound G can be characterized by one or more of the parameters described below in the Methods section (e.g., XRPD, DSC, TGA, and/or DVS).

Propionate Salts of Compound G

In some embodiments, $X^-$ is propionate. A propionate salt of compound G can be characterized by one or more of the parameters described below in the Methods section (e.g., XRPD, DSC, TGA, and/or DVS).

Benzoate Salts of Compound G

In some embodiments, $X^-$ is benzoate. A benzoate salt of compound G can be characterized by one or more of the parameters described below in the Methods section (e.g., XRPD, DSC, TGA, and/or DVS).

Salt Hydrates of Compound G

In some embodiments, the disclosure provides a salt hydrate of compound G, or a free base monohydrate of compound G. The salt hydrate, or free base monohydrate, of compound G can be crystalline, and can be characterized by one or more of the parameters described below in the Methods section (e.g., XRPD, DSC, TGA, and/or DVS).

Methods of Preparing Crystalline Salts, Hydrates, and Salt Hydrates of Compound G The crystalline salts, hydrates, and salt hydrates of compound G can be formed in a variety of ways known in the crystalline arts. Discussion below of crystalline salts of Compound G can apply to formation of crystalline salt hydrates, and to crystalline hydrates of free base Compound G.

In some embodiments, compound G (amorphous form) is admixed with the corresponding acid of the $X^-$ counterion, HX (e.g., maleic acid, fumaric acid, hydrochloric acid, oxalic acid, sulfuric acid, phosphoric acid, malic acid, methanesulfonic acid, 2-naphthalenesulfonic acid, tartaric acid, citric acid, toluenesulfonic acid, propionic acid, benzoic acid), in a solvent to form a suspension. The molar ratio of compound G to HX can be in a range of about 1:05 to about 1:2, such as about 1:1.

The solvent that is added to compound G and HX can be any solvent in which the desired crystalline salts can form. Suitable solvents include, but are not limited to methanol ("MeOH"), ethanol ("EtOH"), isopropanol ("IPA"), ethyl acetate ("EtOAc"), isopropyl acetate ("IPAc"), tetrahydrofuran ("THF"), methyl tert-butyl ether ("MTBE"), acetone/n-heptane, acetone, diethyl ether ("Et$_2$O")/EtOAc, hexane/EtOAc, MTBE/EtOAc, toluene, 1,4-dioxane, acetonitrile ("ACN"), 1-butanol, aqueous mixtures of the foregoing, and combinations thereof. In some embodiments, the solvent includes EtOAc, IPAc, EtOH, aqueous mixtures thereof, or combinations thereof. For example, the solvent can be EtOAc.

The admixing step can occur at a temperature in a range of about 0° C. to 80° C., or about 30° C. to 70° C., or about 40° C. to 60° C. (e.g., about 0, 5, 10, 15, 20, 25, 30, 35, 40, 45, 50, 55, 60, 65, 70, 75, or 80° C.). In some cases, the admixing step occurs at 50° C.

The admixing step can occur for a time period of up to about 6 hours, or up to about 5 hours, or up to about 4 hours, or up to about 3 hours, or up to about 2 hours, or up to about 1 hour. In some embodiments, the admixing step occurs for at least 15 minutes, or at least 30 minutes, or at least 45 minutes, or at least 1 hour, or at least 2 hours, or at least 3 hours, or at least 4 hours, or at least 5 hours. In various cases the admixing step occurs for about 1 hour to about 6 hours, or from about 4 hours to about 6 hours, or from about 3 hours to about 5 hours.

The crystalline salt of compound G can be isolated from the suspension by cooling the suspension to about −10° C. to about 10° C., or to about −5° C. to about 5° C., or to about 0° C. In some embodiments, the cooled suspension can be filtered to form a cake. The cake can then be optionally washed, dried, or both.

In some cases, the crystalline salt of compound G is purified by recrystallization. In various cases, the crystalline salt of compound G is purified by: (i) reforming compound G from the cake, and (ii) admixing the reformed compound G with HX and a solvent to reform the crystalline salt of compound G.

As demonstrated in the Examples section, below, multiple solvents have been identified as useful in the preparation of crystallization salts of compound G, such as monomaleate salts of compound G, in good yield and purity.

Pharmaceutical Compositions and Administration of Crystalline Salts of Compound G Another aspect of the disclosure provides pharmaceutical compositions (alternatively referred to as formulations throughout) that include the crystalline salts described herein and one or more pharmaceutically acceptable excipients. The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The compositions described herein can be formulated for any form of administration.

In some embodiments, the formulations are formulated for parenteral administration. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection, and infusion. For example, parenteral administration can include intravenous, intramuscular, intraperitoneal, or subcutaneous injection. The parenteral pharmaceutical formulations can be liquid formulations or lyophilized formulations that can be reconstituted to a liquid for parenteral injections.

The high solubility of the crystalline salts of compound G described herein make the salts suitable for subcutaneous administration. Subcutaneous administration is an advantageous form of administration because these formulations can be self-administered at home (rather than having to travel to a medical facility for an infusion), which is convenient to patients, and they also have fewer side effects (e.g., less pain at the injection site and bruising) than other types of liquid administration (e.g., intravenous or intramuscular). Both the convenience and decreased side effects of subcutaneous formulations result in better patient compliance. Subcutaneous administration, however, has a practical injection volume limit of about 0.3 to about 1.5 mL, e.g., about 1.0 mL. Therefore, inactive ingredients often need to be included in subcutaneous formulations having high concentrations of the drug substance to deliver a therapeutically effective amount of the drug substance. For example, delivery of about 10 mg to about 100 mg of compound G for the treatment of autoimmune disorders translates to a subcutaneous injection concentration of about 6 mg/ml to about 100 mg/ml. Accordingly, the high solubility of the compound G crystalline salts disclosed herein (exceeding 100 mg/ml) makes them suitable for subcutaneous administration.

Therefore, in some embodiments, the pharmaceutical formulation includes a crystalline salt of compound G at a concentration in a range of about 0.1 mg/ml to about 200 mg/ml, or about 1 mg/ml to about 150 mg/ml, or about 10 mg/ml to about 70 mg/ml, or about 30 mg/ml to about 50 mg/ml, or about 100 mg/mo to about 200 mg/ml, or about 75 mg/ml to about 125 mg/ml. For example, the concentration can be about 30, 40, 50, 60, 70, 80, 90, 100, 110, 120, 130, 140, or 150 mg/ml.

In some embodiments, the one or more excipients includes a surfactant, a tonicity agent, a buffer, or combinations thereof. In embodiments when the formulation is a lyophilized formulation, the one or more excipients can further include a cyroprotectant, a bulking agent, or both. Suitable cryoprotectants include, but are not limited to, glucose, sucrose, trehalose, lactose, mannitol, sorbitol, colloidal silicon dioxide, maltose, poly(vinyl pyrorolidone), fructose, dextran, glycerol, poly(vinyl alcohol), glycine, hydroxyropyl-beta-cyclodextrin, and gelatin. Suitable bulking agents include, but are not limited to, sugars such as mannitol, lactose, sucrose, trehalose, sorbitol, glucose, and raffinose; amino acids such as arginine, glycine, and histidine; and polymers such as dextran and polyethylene glycol.

The one or more excipients can include a surfactant, such as a nonionic surfactant. Nonionic surfactants can be useful in stabilizing the formulation from degradation due to shipping stress and storage. Suitable surfactants for inclusion in pharmaceutical formulations include, but are not limited to, polysorbates and polyethers. For example, the surfactant can include polysorbate (e.g., polysorbate 80 or polysorbate 20), polyoxyl castor oil, poly(alkylene)glycol (e.g., polyethylene glycol, polypropylene glycol), caprylocaproyl polyoxylglyceride, polyoxyalkylene block copolymer (e.g, polyoxyethylene-polyoxypropylene), and combinations thereof. In some embodiments, the surfactant can further include a co-solvent, such as N-methyl-2-pyrrolidone ("NMP").

The one or more excipients can include a tonicity agent (sometimes referred to as an isotonic agent). Tonicity agents can be included in subcutaneous formulations to ensure that the formulation has an osmolality that matches a patient's cells (e.g., 250 to 350 mOsm) to minimize or prevent tissue damage at the injection site. Tonicity agents include salts and polyols (e.g., sugars such as nonreducing sugars, sugar alcohols, and sugar acids). Specifically contemplated tonicity agents include, but are not limited to, NaCl, KCl, glucose, fructose, saccharose, maltose, lactose, sucrose, mannose, raffinose, mannitol, xylitol, galactitol, glucitol, inositol, sorbitol, trehalose and glycerine. Accordingly, also provided herein are pharmaceutical formulations that are isotonic.

The one or more excipients can include a buffer. Pharmaceutically acceptable buffers include, but are not limited to, citrate, phosphate, histidine, succinate, acetate, maleate, gluconate, and combinations thereof. In some embodiments, the pH of the formulation is in a range of about 3.0 to 8.0, or about 4.0 to 7.0, or about 4.0 to 6.5.

The formulations of the crystalline salts disclosed herein can be administered to a subject, such as a human subject or an animal subject. In some embodiments, these formulations exhibit a bioavailability of at least about 45%, or at least about 50%, or at least about 55%, or at least about 60%, or at least about 65%, or at least about 70%. In some cases, the formulations disclosed herein exhibit a bioavailability of up to about 90%, or up to about 85%, or up to about 80%, or up to about 75%, or up to about 65%, or up to about 60%. For example, the formulations can exhibit a bioavailability of about 45% to about 90%, or about 50% to about 70%, or about 50% to about 65%.

The crystalline salts disclosed herein also can be formulated into pharmaceutical compositions having the forms and including the excipients described in detail, below.

In some embodiments, the pharmaceutical compositions can include a pharmaceutically acceptable carrier. The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20)phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions as excipients.

Examples of pharmaceutically acceptable antioxidants as excipient include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A pharmaceutical composition may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

In some cases, in order to prolong the effect of one or more compounds provided herein, it is desirable to slow the absorption of the compound from subcutaneous or intramuscular injection. For example, delayed absorption of a parenterally administered compound can be accomplished by dissolving or suspending the compound in an oil vehicle.

The composition should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the methods of preparation are freeze-drying (lyophilization), which yields a powder of the active ingredient plus any additional desired ingredient from a previously sterile-filtered solution thereof.

Injectable depot forms can be made by forming microencapsule or nanoencapsule matrices of a compound provided herein in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes, microemulsions or nanoemulsions, which are compatible with body tissue.

In one embodiment, the therapeutic crystalline salts are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811, which is incorporated herein by reference in its entirety.

The pharmaceutical compositions can be included in a container, pack, or dispenser together with instructions for administration.

Methods of Using Crystalline Salts of Compound G

The crystalline salts disclosed herein can act as inhibitors of immunoproteasome (iP). In some cases, the crystalline salts disclosed herein inhibit the iP subunit LMP7. LMP7 activity can be inhibited by at least 10%, at least 20%, at least 30%, at least 40%, at least 50%, at least 60%, at least 70%, or at least 80%, as measured in a proteasome subunit assay as described below in the examples. One or more additional iP subunits can be inhibited by a crystalline salt disclosed herein, such as LMP2, MECL-1, β1, β2, and β5. In various embodiments, a crystalline salt disclosed herein inhibits LMP7 and one or both of LMP2 and MECL-1. The compounds disclosed herein can reduce cytokine activity or expression, e.g., one or more of IL-2, MHC-I, IL-6, TNFα, and IFN-β. Thus, provided are methods wherein a compound as disclosed herein inhibits expression or activity of one or more of IL-2, MHC-I, IL-6, TNFα, and IFN-β by at least 10%, at least 20%, at least 30%, at least 40%, at least 50%, at least 60%, at least 70%, or at least 80%.

Further provided herein are methods of inhibiting immunoproteasome in a cell by contacting the cell with one or more of the crystalline salts, or compositions thereof, described herein. In some embodiments, the immunoproteasome LMP7 subunit is inhibited. The contacting step described herein can occur in vivo or in vitro.

The biological consequences of proteasome inhibition are numerous. Proteasome inhibition has been suggested as a prevention and/or treatment of a multitude of diseases including, but not limited to, neurotoxic/degenerative diseases, Alzheimer's, ischemic conditions, inflammation, auto-immune diseases, HIV, organ graft rejection, septic shock, inhibition of antigen presentation, decreasing viral gene expression, parasitic infections, conditions associated with acidosis, macular degeneration, pulmonary conditions, muscle wasting diseases, fibrotic diseases, and bone and hair growth diseases. Therefore, pharmaceutical formulations containing the crystalline salts described herein provide a means of administering the salts to a patient to treat these conditions.

Accordingly, the contacting step of the methods disclosed herein can include administering one or more of the crystalline salts, or compositions thereof, described herein to a subject who suffers from a disorder associated with aberrant immunoproteasome activity. As described in further detail, below, the disorder can be an autoimmune disease or inflammation. In some embodiments, the disease can be psoriasis, dermatitis, systemic scleroderma, sclerosis, Crohn's disease, ulcerative colitis; respiratory distress syndrome, meningitis; encephalitis; uveitis; colitis; glomerulonephritis; eczema, asthma, chronic inflammation; atherosclerosis; leukocyte adhesion deficiency; rheumatoid arthritis; systemic lupus erythematosus (SLE); diabetes mellitus; multiple sclerosis; Reynaud's syndrome; autoimmune thyroiditis; allergic encephalomyelitis; Sjogren's syndrome; juvenile onset diabetes; tuberculosis, sarcoidosis, polymyositis, granulomatosis, vasculitis; pernicious anemia (Addison's disease); a disease involving leukocyte diapedesis; central nervous system (CNS) inflammatory disorder; multiple organ injury syndrome; hemolytic anemia; myasthenia gravis; antigen-antibody complex mediated disease; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Beheet disease; giant cell arteritis; immune complex nephritis; IgA nephropathy; IgM polyneuropathies; immune thrombocytopenic purpura (ITP) or autoimmune thrombocytopenia. In some cases, the disorder can be lupus, lupus nephritis, rheumatoid arthritis, diabetes, scleroderma, ankylosing spondylitis, psoriasis, multiple sclerosis, Hashimoto's disease, meningitis, or inflammatory bowel disease.

The proteasome regulates NF-κB, which in turn regulates genes involved in the immune and inflammatory response. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β (Palombella et al., *Cell* (1994) 78:773-785). Thus, provided herein are methods of affecting the level of expression of IL-2, MHC-I, IL-6, TNFα, IFN-β or any of the other previously-mentioned proteins, each method comprising administering to a patient a therapeutically effective amount of a crystalline salt or composition disclosed herein.

Also provided herein is a method of treating an autoimmune disease in a patient comprising administering a therapeutically effective amount of the crystalline salt described herein. An "autoimmune disease" as used herein is a disease or disorder arising from and directed against an individual's own tissues. Examples of autoimmune diseases include, but are not limited to, inflammatory responses such as inflammatory skin diseases including psoriasis and dermatitis (e.g., atopic dermatitis); systemic scleroderma and sclerosis; responses associated with inflammatory bowel disease (such as Crohn's disease and ulcerative colitis); respiratory distress syndrome (including adult respiratory distress syndrome (ARDS)); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g., Type I diabetes mellitus or insulin dependent diabetes mellitus); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Beheet disease; giant cell arteritis; immune complex nephritis; IgA nephropathy; IgM polyneuropathies; immune thrombocytopenic purpura (ITP) or autoimmune thrombocytopenia.

The immune system screens for autologous cells that are virally infected, have undergone oncogenic transformation or present unfamiliar peptides on their surface. Intracellular proteolysis generate small peptides for presentation to T-lymphocytes to induce MHC class I-mediated immune responses. Thus, provided herein is a method of using a crystalline salt or composition provided herein as an immunomodulatory agent for inhibiting or altering antigen presentation in a cell, comprising exposing the cell (or administering to a patient) to the compound described herein. Specific embodiments include a method of treating graft or transplant-related diseases, such as graft-versus-host disease or host versus-graft disease in a patient, comprising administering a therapeutically effective amount of the compound described herein. The term "graft" as used herein refers to biological material derived from a donor for transplantation into a recipient. Grafts include such diverse material as, for example, isolated cells such as islet cells; tissue such as the amniotic membrane of a newborn; bone marrow; hematopoietic precursor cells; ocular tissue, such as corneal tissue; and organs such as skin, heart, liver, spleen, pancreas, thyroid lobe, lung, kidney, and tubular organs (e.g., intestine, blood vessels, or esophagus). The tubular organs can be used to replace damaged portions of esophagus, blood vessels, or bile duct. The skin grafts can be used not only for burns, but also as a dressing to damaged intestine or to close certain defects such as diaphragmatic hernia. The graft is derived from any mammalian source, including human, whether from cadavers or living donors. In some cases, the donor and recipient is the same patient. In some embodiments, the graft is bone marrow or an organ such as heart and the donor of the graft and the host are matched for HLA class II antigens.

Proteasome inhibition has also been associated with inhibition of NF-κB activation and stabilization of p53 levels. Thus, crystalline salts and compositions thereof provided herein may also be used to inhibit NF-κB activation, and stabilize p53 levels in cell culture. Since NF-κB is a key regulator of inflammation, it is an attractive target for anti-inflammatory therapeutic intervention. Thus, crystalline salts and compositions thereof provided herein may be useful for the treatment of conditions associated with inflammation, including, but not limited to COPD, psoriasis, asthma, bronchitis, emphysema, and cystic fibrosis.

The disclosed crystalline salts and compositions thereof can be used to treat conditions mediated directly by the proteolytic function of the proteasome such as muscle wasting, or mediated indirectly via proteins which are processed by the proteasome such as NF-κB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include β-amyloid protein and regulatory proteins such as cyclins and transcription factor NF-κB.

In some embodiments, a crystalline salt or composition thereof provided herein is useful for the treatment of neurodegenerative diseases and conditions, including, but not limited to, stroke, ischemic damage to the nervous system, neural trauma (e.g., percussive brain damage, spinal cord injury, and traumatic damage to the nervous system), multiple sclerosis, and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

Alzheimer's disease is characterized by extracellular deposits of β-amyloid protein (β-AP) in senile plaques and cerebral vessels. β-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes to the abundance of β-AP in the Alzheimer brain. The APP-processing enzyme in rats contains about ten different subunits (22 kDa-32 kDa). The 25 kDa subunit has an N-terminal sequence of X⁻ Gln-Asn-Pro-Met-X-Thr-Gly-Thr-Ser, which is identical to the β-subunit of human macropain (Kojima, S. et al., *Fed. Eur. Biochem. Soc.*, (1992) 304:57-60). The APP-processing enzyme cleaves at the Gln15-Lys16 bond; in the presence of calcium ion, the enzyme also cleaves at the Met-1-Asp1 bond, and the Asp1-Ala2 bonds to release the extracellular domain of β-AP.

Therefore, provided herein is a method of treating Alzheimer's disease, including administering to a patient a therapeutically effective amount of a crystalline salt or composition thereof disclosed herein. Such treatment includes reducing the rate of β-AP processing, reducing the rate of β-AP plaque formation, reducing the rate of β-AP generation, and reducing the clinical signs of Alzheimer's disease.

Also provided herein are methods of treating cachexia and muscle-wasting diseases. The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver. Peptide proteasome inhibitors (e.g., a compound or composition provided herein) are useful for treating conditions such as chronic infectious diseases, fever, muscle disuse (atrophy) and denervation, nerve injury, fasting, renal failure associated with acidosis, kidney disease, and hepatic failure. See, e.g., Goldberg, U.S. Pat. No. 5,340,736, which is incorporated herein by reference in its entirety. Methods of treatment include: reducing the rate of muscle protein degradation in a cell; reducing the rate of intracellular protein degradation; and reducing the rate of degradation of p53 protein in a cell. Each of these methods includes contacting a cell (in vivo or in vitro, e.g., a muscle in a patient) with an effective amount of a pharmaceutical composition disclosed herein to reduce the rate of muscle protein degradation in the cell; reduce the rate of intracellular protein degradation in the cell; and/or reduce the rate of degradation of p53 protein in the cell. In some embodiments, the methods include administering to a patient a therapeutically effective amount of a crystalline salt or pharmaceutical composition thereof disclosed herein.

Fibrosis is the excessive and persistent formation of scar tissue resulting from the hyperproliferative growth of fibroblasts and is associated with activation of the TGF-β signaling pathway. Fibrosis involves extensive deposition of extracellular matrix and can occur within virtually any tissue or across several different tissues. Normally, the level of intracellular signaling protein (Smad) that activates transcription of target genes upon TGF-β stimulation is regulated by proteasome activity. However, accelerated degradation of the TGF-β signaling components has been observed in hyperproliferative conditions. Thus, in certain embodiments, a method for treating hyperproliferative conditions such as diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstitial lung diseases, and extrinsic lung disorders) is provided. The treatment of burn victims is often hampered by fibrosis, thus, in some embodiments a compound provided herein may be administered by topical or systemic administration to treat burns. Wound closure following surgery is often associated with disfiguring scars, which may be prevented by inhibition of fibrosis. Thus, in certain embodiments, a method for the prevention or reduction of scarring is provided herein by administering a crystalline salt or composition thereof disclosed herein.

Another protein processed by the proteasome is NF-κB, a member of the Rel protein family. The Rel family of transcriptional activator proteins can be divided into two groups. The first group requires proteolytic processing, and includes p50 (NF-κB1, 105 kDa) and p52 (NF-κ2, 100 kDa). The second group does not require proteolytic processing, and includes p65 (RelA, Rel (c-Rel), and RelB). Both homo- and heterodimers can be formed by Rel family members; NF-κB, for example, is a p50-p65 heterodimer. After phosphorylation and ubiquitination of IκB and p105, the two proteins are degraded and processed, respectively, to produce active NF-κB which translocates from the cytoplasm to the nucleus. Ubiquitinated p105 is also processed by purified proteasomes (Palombella et al., Cell (1994) 78:773-785). Active NF-κB forms a stereospecific enhancer complex with other transcriptional activators and, e.g., HMG I(Y), inducing selective expression of a particular gene.

NF-κB regulates genes involved in the immune and inflammatory response, and mitotic events. For example, NF-κB is required for the expression of the immunoglobulin light chain x gene, the IL-2 receptor α-chain gene, the class I major histocompatibility complex gene, and a number of cytokine genes encoding, for example, IL-2, IL-6, granulocyte colony-stimulating factor, and IFN-0 (Palombella et al., Cell (1994) 78:773-785). Some embodiments include methods of affecting the level of expression of IL-2, MHC-I, IL-6, TNFα, IFN-β, or any of the other previously-mentioned proteins, each method including administering to a patient a therapeutically effective amount of a crystalline salt or composition thereof disclosed herein. Complexes including p50 are rapid mediators of acute inflammatory and immune responses (Thanos, D. and Maniatis, T., Cell (1995) 80:529-532).

NF-κB also participates in the expression of the cell adhesion genes that encode E-selectin, P-selectin, ICAM, and VCAM-1 (Collins, T., Lab. Invest. (1993) 68:499-508). In some embodiments, a method for inhibiting cell adhesion (e.g., cell adhesion mediated by E-selectin, P-selectin, ICAM, or VCAM-1) is provided, including contacting a cell with an effective amount of a crystalline salt or pharmaceutical composition thereof disclosed herein. In some embodiments, a method for inhibiting cell adhesion (e.g., cell adhesion mediated by E-selectin, P-selectin, ICAM, or VCAM-1) is provided, including administering to a patient a therapeutically effective amount of a pharmaceutical composition disclosed herein.

Ischemia and reperfusion injury results in hypoxia, a condition in which there is a deficiency of oxygen reaching the tissues of the body. This condition causes increased degradation of Iκ-Bα, thereby resulting in the activation of NF-κB. It has been demonstrated that the severity of injury resulting in hypoxia can be reduced with the administration of a proteasome inhibitor. Thus, provided herein is a method of treating an ischemic condition or reperfusion injury comprising administering to a patient in need of such treatment a therapeutically effective amount of a crystalline salt or composition thereof provided herein. Examples of such conditions or injuries include, but are not limited to, acute coronary syndrome (vulnerable plaques), arterial occlusive disease (cardiac, cerebral, peripheral arterial, and vascular occlusions), atherosclerosis (coronary sclerosis, coronary artery disease), infarctions, heart failure, pancreatitis, myocardial hypertrophy, stenosis, and restenosis.

NF-κB also binds specifically to the HIV-enhancer/promoter. When compared to the Nef of mac239, the HIV regulatory protein Nef of pbj 14 differs by two amino acids in the region which controls protein kinase binding. It is believed that the protein kinase signals the phosphorylation of IκB, triggering IκB degradation through the ubiquitin-proteasome pathway. After degradation, NF-κB is released into the nucleus, thus enhancing the transcription of HIV (Cohen, J., Science, (1995) 267:960). Provided herein is a method for inhibiting or reducing HIV infection in a patient, and a method for decreasing the level of viral gene expression, each method including administering to the patient a therapeutically effective amount of a crystalline salt or composition thereof disclosed herein.

Viral infections contribute to the pathology of many diseases. Heart conditions such as ongoing myocarditis and dilated cardiomyopathy have been linked to the coxsackievirus B3. In a comparative whole-genome microarray analyses of infected mouse hearts, specific proteasome subunits were uniformly up-regulated in hearts of mice which developed chronic myocarditis (Szalay et al, Am J Pathol 168:1542-52, 2006). Some viruses utilize the ubiquitin-proteasome system in the viral entry step where the virus is released from the endosome into the cytosol. The mouse hepatitis virus (MHV) belongs to the Coronaviridae family, which also includes the severe acute respiratory syndrome (SARS) coronavirus. Yu and Lai (J Virol 79:644-648, 2005) demonstrated that treatment of cells infected with MHV with a proteasome inhibitor resulted in a decrease in viral replication, correlating with reduced viral titer as compared to that of untreated cells. The human hepatitis B virus (HBV), a member of the Hepadnaviridae virus family, likewise requires virally encoded envelop proteins to propagate. Inhibiting the proteasome degradation pathway causes a significant reduction in the amount of secreted envelope proteins (Simsek et al, J Virol 79:12914-12920, 2005). In addition to HBV, other hepatitis viruses (A, C, D and E) may also utilize the ubiquitin-proteasome degradation pathway for secretion, morphogenesis and pathogenesis. Accordingly, in certain embodiments, a method for treating viral infection, such as SARS or hepatitis A, B, C, D and E, is provided comprising contacting a cell with an effective amount of a crystalline salt or composition thereof disclosed herein. In some embodiments, a method for treating viral infection, such as SARS or hepatitis A, B, C, D and E, is provided comprising administering to a patient a therapeutically effective amount of the crystalline salt or composition thereof disclosed herein.

Overproduction of lipopolysaccharide (LPS)-induced cytokines such as TNFα is considered to be central to the processes associated with septic shock. Furthermore, it is generally accepted that the first step in the activation of cells by LPS is the binding of LPS to specific membrane receptors. The α- and β-subunits of the 20S proteasome complex have been identified as LPS-binding proteins, suggesting that the LPS-induced signal transduction may be an important therapeutic target in the treatment or prevention of sepsis (Qureshi, N. et al., *J. Immun.* (2003) 171: 1515-1525). Therefore, in certain embodiments, crystalline salts and compositions thereof, as provided herein, may be used for the inhibition of TNFα to prevent and/or treat septic shock.

Intracellular proteolysis generates small peptides for presentation to T-lymphocytes to induce MHC class I-mediated immune responses. The immune system screens for autologous cells that are virally infected or have undergone oncogenic transformation. One embodiment is a method for inhibiting antigen presentation in a cell, including exposing the cell to a composition described herein. In some embodiments, the cell is contacted with an effective amount of a compound or composition provided herein to inhibit antigen presentation in the cell. A further embodiment is a method for suppressing the immune system of a patient (e.g., inhibiting transplant rejection, allergy, asthma), including administering to the patient a therapeutically effective amount of a composition described herein. Crystalline salts and compositions provided herein can also be used to treat autoimmune diseases such as lupus, rheumatoid arthritis, multiple sclerosis, and inflammatory bowel diseases such as ulcerative colitis and Crohn's disease.

Another embodiment is a method for altering the repertoire of antigenic peptides produced by the proteasome or other Ntn with multicatalytic activity. For example, if the PGPH activity of 20S proteasome is selectively inhibited, a different set of antigenic peptides will be produced by the proteasome and presented in MHC molecules on the surfaces of cells than would be produced and presented either without any enzyme inhibition, or with, for example, selective inhibition of chymotrypsin-like activity of the proteasome.

Certain proteasome inhibitors block both degradation and processing of ubiquitinated NF-κB in vitro and in vivo. Proteasome inhibitors also block IκB-α degradation and NF-κB activation (Palombella, et al. *Cell* (1994) 78:773-785; and Traenckner, et al., EMBO J. (1994) 13:5433-5441). In some embodiments, a method for inhibiting IκB-α degradation is provided, including contacting a cell with a crystalline salt or composition thereof described herein. In some embodiments, a cell is contacted with an effective amount of the crystalline salt or composition thereof to inhibit IκB-α degradation. A further embodiment is a method for reducing the cellular content of NF-κB in a cell, muscle, organ, or patient, including contacting the cell, muscle, organ, or patient with a crystalline salt or composition thereof described herein. In some embodiments, a cell is contacted with an effective amount of the composition to reduce the cellular content of NF-κB in a cell.

Other eukaryotic transcription factors that require proteolytic processing include the general transcription factor TFIIA, herpes simplex virus VP16 accessory protein (host cell factor), virus-inducible IFN regulatory factor 2 protein, and the membrane-bound sterol regulatory element-binding protein 1.

Further provided herein are methods for affecting cyclin-dependent eukaryotic cell cycles, including exposing a cell (in vitro or in vivo) to a composition disclosed herein. Cyclins are proteins involved in cell cycle control. The proteasome participates in the degradation of cyclins. Examples of cyclins include mitotic cyclins, G1 cyclins, and cyclin B. Degradation of cyclins enables a cell to exit one cell cycle stage (e.g., mitosis) and enter another (e.g., division). It is believed that all cyclins are associated with p34cdc2 protein kinase or related kinases. The proteolysis targeting signal is localized to amino acids 42-RAAL-GNISEN-50 (destruction box). There is evidence that cyclin is converted to a form vulnerable to a ubiquitin ligase or that a cyclin-specific ligase is activated during mitosis (Ciechanover, A., Cell, (1994) 79:13-21). Inhibition of the proteasome inhibits cyclin degradation, and therefore inhibits cell proliferation (Kumatori et al., Proc. Natl. Acad. Sci. USA (1990) 87:7071-7075). Provided herein is a method for treating a proliferative disease in a patient (e.g., psoriasis or restenosis), including administering to the patient a therapeutically effective amount of a crystalline salt or composition thereof disclosed herein. Also provided herein is a method for treating cyclin-related inflammation in a patient, including administering to a patient a therapeutically effective amount of a crystalline salt or composition thereof described herein.

In another embodiment, the disclosed compositions are useful for the treatment of a parasitic infection, such as infections caused by protozoan parasites. The proteasome of these parasites is considered to be involved primarily in cell differentiation and replication activities (Paugam et al., *Trends Parasitol.* 2003, 19(2): 55-59). Furthermore, entamoeba species have been shown to lose encystation capacity when exposed to proteasome inhibitors (Gonzales, et al., *Arch. Med. Res.* 1997, 28, Spec No: 139-140). In certain such embodiments, the disclosed crystalline salts and compositions thereof are useful for the treatment of parasitic infections in humans caused by a protozoan parasite selected from Plasmodium sps. (including P. falciparum, P. vivax, P. malariae, and P. ovale, which cause malaria), Trypanosoma sps. (including T. cruzi, which causes Chagas' disease, and T. brucei which causes African sleeping sickness), Leishmania sps. (including L. amazonesis, L. donovani, L. infantum, L. mexicana, etc.), Pneumocystis carinii (a protozoan known to cause pneumonia in AIDS and other immunosuppressed patients), Toxoplasma gondii, Entamoeba histolytica, Entamoeba invadens, and Giardia lamblia. In certain embodiments, the disclosed crystalline salts and compositions thereof are useful for the treatment of parasitic infections in animals and livestock caused by a protozoan parasite selected from Plasmodium hermani, Cryptosporidium sps., Echinococcus granulosus, Eimeria tenella, Sarcocystis neurona, and *Neurospora crassa*. Other compounds useful as proteasome inhibitors in the treatment of parasitic diseases are described in WO 98/10779, which is incorporated herein in its entirety.

In certain embodiments, the disclosed crystalline salts and compositions thereof inhibit proteasome activity irreversibly in a parasite. Such irreversible inhibition has been shown to induce shutdown in enzyme activity without recovery in red blood cells and white blood cells. In certain such embodiments, the long half-life of blood cells may provide prolonged protection with regard to therapy against recurring exposures to parasites. In certain embodiments, the long half-life of blood cells may provide prolonged protection with regard to chemoprophylaxis against future infection.

Prokaryotes have what is equivalent to the eukaryote 20S proteasome particle. Albeit, the subunit composition of the prokaryote 20S particle is simpler than that of eukaryotes, it has the ability to hydrolyze peptide bonds in a similar manner. For example, the nucleophilic attack on the peptide bond occurs through the threonine residue on the N-terminus of the β-subunits. In some embodiments, a method of treating prokaryotic infections is provided, comprising administering to a patient a therapeutically effective amount of a crystalline salt or composition thereof provided herein. Prokaryotic infections may include diseases caused by either mycobacteria (such as tuberculosis, leprosy or Buruli Ulcer) or archaebacteria.

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett, I. R. et al., *J. Clin. Invest.* (2003) 111: 1771-1782), therefore suggesting that the ubiquitin-proteasome machinery regulates osteoblast differentiation and bone formation. Therefore, the disclosed crystalline salts and compositions thereof may be useful in the treatment and/or prevention of diseases associated with bone loss, such as osteoporosis.

Provided herein is a method for treating a disease or condition selected from autoimmune disease, graft or transplant-related condition, neurodegenerative disease, fibrotic-associated condition, ischemic-related conditions, infection (viral, parasitic or prokaryotic), and diseases associated with bone loss, comprising administering a crystalline salt or composition thereof as provided herein.

Bone tissue is an excellent source for factors which have the capacity for stimulating bone cells. Thus, extracts of bovine bone tissue contain not only structural proteins which are responsible for maintaining the structural integrity of bone, but also biologically active bone growth factors which can stimulate bone cells to proliferate. Among these latter factors are a recently described family of proteins called bone morphogenetic proteins (BMPs). All of these growth factors have effects on other types of cells, as well as on bone cells, including Hardy, M. H., et al., *Trans Genet* (1992) 8:55-61 describes evidence that bone morphogenetic proteins (BMPs), are differentially expressed in hair follicles during development. Harris, S. E., et al., *J Bone Miner Res* (1994) 9:855-863 describes the effects of TGF-β on expression of BMP-2 and other substances in bone cells. BMP-2 expression in mature follicles also occurs during maturation and after the period of cell proliferation (Hardy, et al. (1992, supra). Thus, crystalline salts and compositions thereof provided herein may also be useful for hair follicle growth stimulation.

Also provided herein is a method for treating a lysosomal storage disorder by administration of a compound as disclosed herein. Lysosomal storage disorders are a group of diseases resulting from the abnormal metabolism of various substrates, including glycosphingolipids, glycogen, mucopolysaccharides, and glycoproteins. The metabolism of exo- and endogenous high molecular weight compounds normally occurs in the lysosomes, and the process is normally regulated in a stepwise process by degradation enzymes. Therefore, a deficient activity in one enzyme may impair the process, resulting in an accumulation of particular substrates. It has been shown that inhibition of the proteasome can improve the function of certain substrates in patients suffering from a lysosomal storage disorder (Y. Shimada et al. *Biochem. Biophys. Res. Commun.* (2011) 415(2):274-8). Most of these diseases can be clinically classified into subtypes: i) infantile-onset; ii) juvenile-onset; or iii) late-onset. The infantile-onset forms are often the most severe usually with no residual enzyme activity. The later-onset forms are often milder with low, but often detectable residual enzyme activity. The severity of the juvenile-onset forms are in between the infantile-onset and late-onset forms. Non-limiting examples of such disorders include: Pompe disease, Gaucher disease, Fabry disease, GM1-gangliosidosis, Tay-Sachs disease, Sandhoff disease, Niemann-Pick disease, Krabbe disease, Farber disease, Metachromatic leukodystrophy, Hurler-Scheie disease, Hunter disease, Sanfilippo disease A, Sanfilippo disease B, Sanfilippo disease C, Sanfilippo disease D, Morquio disease A, Morquio disease B, Maroteaux-Lamy disease, Sly disease, α-mannosidosis, β-mannosidosis, fucosidosis, sialidosis, and Schindler-Kanzaki disease. One embodiment, therefore, is a method of treating Pompe disease, including administering to a patient a therapeutically effective amount of a crystalline salt or composition thereof provided herein.

The disclosed crystalline salts and compositions thereof are also useful as diagnostic agents (e.g., in diagnostic kits or for use in clinical laboratories) for screening for proteins (e.g., enzymes, transcription factors) processed by Ntn hydrolases, including the proteasome. The disclosed crystalline salts and compositions thereof are also useful as research reagents for specifically binding the X/MB 1 subunit or α-chain and inhibiting the proteolytic activities associated with it. For example, the activity of (and specific inhibitors of) other subunits of the proteasome can be determined.

Most cellular proteins are subject to proteolytic processing during maturation or activation. Enzyme inhibitors disclosed herein can be used to determine whether a cellular, developmental, or physiological process or output is regulated by the proteolytic activity of a particular Ntn hydrolase. One such method includes obtaining an organism, an intact cell preparation, or a cell extract; exposing the organism, cell preparation, or cell extract to a composition disclosed herein; exposing the compound-exposed organism, cell preparation, or cell extract to a signal; and monitoring the process or output. The high selectivity of the compounds disclosed herein permits rapid and accurate elimination or implication of the Ntn (for example, the 20S proteasome) in a given cellular, developmental, or physiological process.

EXAMPLES

The following examples are provided for illustration and are not intended to limit the scope of the invention Example 1: Characterization Methods X-ray powder diffraction ("XRPD") data were obtained on a PANalytical X'Pert3 X⁻ ray (FIGS. 1, 21, and 22-27), Shimadzu XRD-7000 (FIG. 5), or Bruker D8Advance X-ray Powder Diffractometer (FIGS. 1, 9, 11, 13-15, and 19). Samples were scanned in continuous mode from 4-40° (2θ) with a step size of 0.02° at 40 kV and 40 mA with CuKα radiation (1.54 Å) (FIG. 1). Samples were scanned in continuous mode from 3-40° (2θ) with a step size of 0.0130 at 45 kV and 40 mA with CuKα radiation (1.54 Å) (FIGS. 21 and 23-27). Samples were scanned in continuous mode from 5-70° (2θ) with a step size of 0.02° at 40 kV and 35 mA with CuKα radiation (1.54 Å) (FIG. 5). Samples were scanned in continuous mode from 3-40° (2θ) with a step size of 0.020 at 40 kV and 40 mA with CuKα radiation (1.54 Å) (FIGS. 1, 9, 11, 13-15, and 19).

Differential scanning calorimetry ("DSC") was performed on a TA Instruments Q2000 calorimeter in an aluminum crimped pan (FIG. 22), TA Q20 DSC in a Tzero Low-Mass Pan (FIG. 2), or TA Instruments Q20 in an aluminum Tzero Pan (FIG. 6), or Dynamic Vapor Sorption Advantage System using a crimped aluminum pan (FIGS. 8, 10, 12, 16, 17, and 20) under dry nitrogen.

Thermogravimetric analysis (TGA) was performed on a TA Instruments Q500 analyzer (FIG. 22) or NETZSCH TG209 F1 (FIG. 3) in a platinum pan (FIG. 22) or aluminum Tzero pan (FIG. 3) under dry nitrogen.

Figure 18:
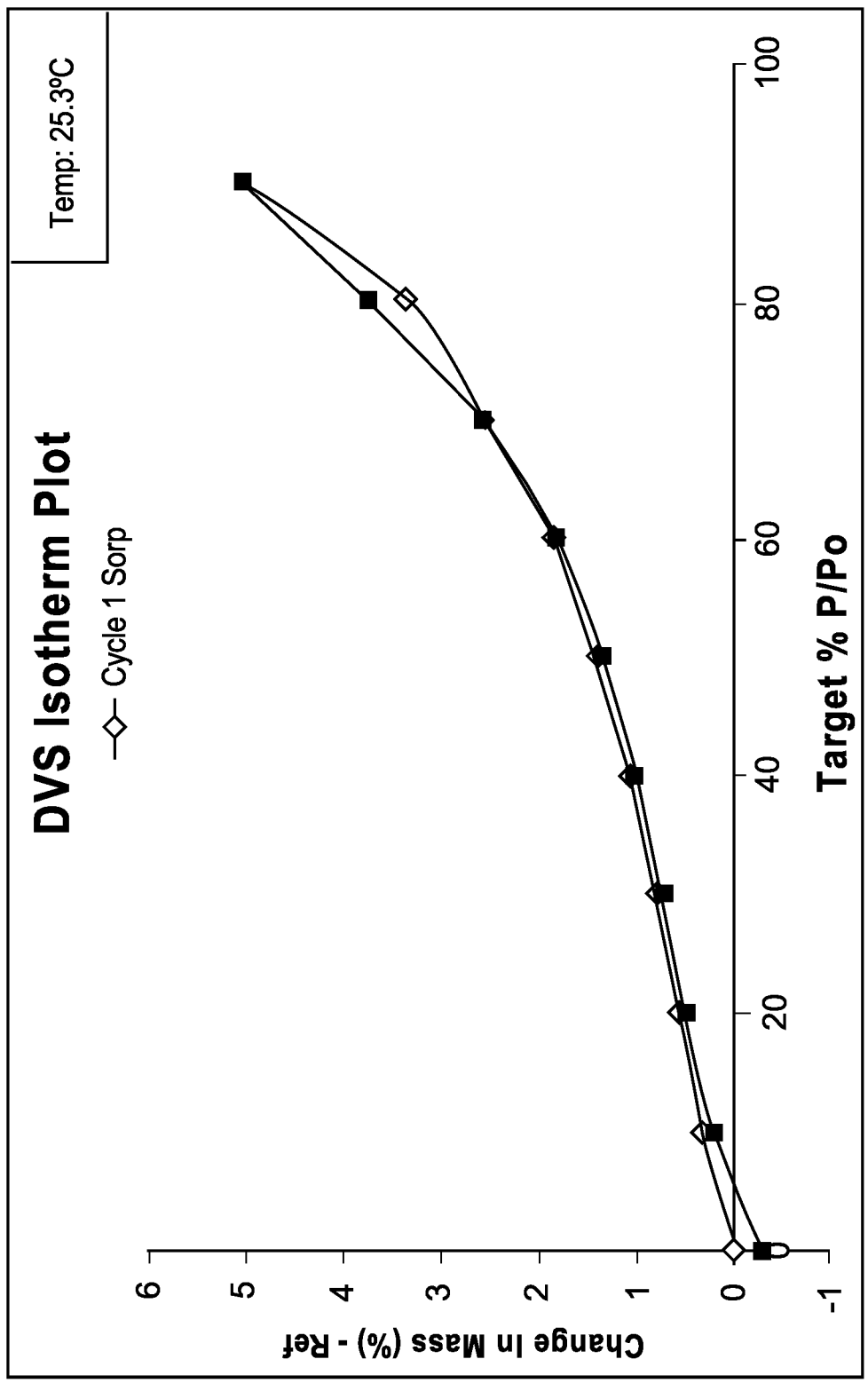
FIG. 18 depicts the dynamic vapor sorption ("DVS") isotherm plot of Form B (monomaleate hydrate of compound G prepared in 3% water/acetone)

Moisture sorption data was collected using a SMS (Surface Measurement Systems) DVSIntrinsic (FIG. 4) or Dynamic Vapor Sorption Advantage System (FIG. 18). Equilibrium criteria were set at ±0.002% (FIG. 4) weight change in 10 minutes with a maximum equilibrium time of 180 minutes.

$^1$H NMR was performed on a Varian 400 MHz instrument. Solid samples were dissolved in DMSO-d6 and transferred to NMR tubes for analysis.

Example 2: Salt Screening of Compound G

Compound G was reacted with six different acids, each in six different solvent systems (a total of 36 screening experiments) to determine whether a crystalline salt of compound G could be formed.

In particular, about 15 mg of compound G and an equivalent molar amount of an acid were admixed into a 2.0 mL glass vial. About 1.0 mL of a corresponding solvent system was added to the vial. The resulting suspensions were stirred at approximately 600 rpm at room temperature for about two days. The suspensions were then centrifuged to isolate the solids for XRPD analysis. The results of the screening experiments can be found in Table 3. Of the six acids tested, two resulted in the formation of a crystalline salt of compound G: maleic acid and fumaric acid.

TABLE 3

Results for Salt Screening of Compound G

| | | Solvent | | | | | |
|---|---|---|---|---|---|---|---|
| | Acids | IPA | EtOAc | THF | MTBE | Acetone/n-heptane | EtOH/H2O |
| 1 | HCl | clear | clear | clear | clear | clear | clear |
| 2 | H$_3$PO$_4$ | clear | clear | clear | clear | clear | clear |
| 3 | maleic acid | maleate salt crystals | maleate salt crystals | maleate salt crystals | maleate salt crystals | maleate salt crystals | clear |
| 4 | fumaric acid | clear | fumarate salt crystals Form G | clear | fumarate salt crystals Form G | fumarate salt crystals Form G | clear |
| 5 | L-tartric acid | clear | clear | clear | clear | clear | clear |
| 6 | citric acid | clear | clear | clear | clear | clear | clear |

Clear: no or limited solid was precipitated out.

Example 3: Additional Salt Screening of Compound G

To Compound G (20 mg, pre-dissolved in 140 μL of solvent) was added 1 equivalent of acid (pre-dissolved in 40-240 μL in solvent) and the mixtures were allowed to stand over 96 h in a sealed vial. The following solvents were employed: toluene, ethanol, methanol, isopropanol, hexane/ethyl acetate (1:1), 1,4-dioxane, acetonitrile, 1-butanol, ethyl acetate, acetone, MTBE/ethyl acetate (1:1), and diethyl ether/ethyl acetate (1:1). The following acids were utilized: sulfuric, methanesulfonic, tosylic (monohydrate), 2-napthalenesulfonic, L-malic, propionic, benzoic, oxalic, and phosphoric. Solid precipitate was observed with the combinations shown in Table 4.

TABLE 4

Salt Screening Variables

| Acid | Solvent System |
|---|---|
| Sulfuric Acid | Et$_2$O/EtOAc |
| 1-Naphthalenesulfonic acid | Hexane/EtOAc |
| | MTBE/EtOAc |
| Oxalic Acid | Toluene |
| | Hexane/EtOAc |
| | MTBE/EtOAc |
| | Et$_2$O/EtOAc |
| Phosphoric Acid | Hexane/EtOAc |
| | MTBE/EtOAc |
| | Et$_2$O/EtOAc |
| L-Malic Acid | Hexane/EtOAc |

Example 4: Scale-Up of Compound G Maleate Salt

The preparation of the monomaleate form of compound G was scaled up as follows. Compound G (about 200 mg) was reacted with maleic acid at a molar ratio of 1:1 or 1:2 by weighing both starting materials into a glass vial. A volume of MTBE or acetone was added to each glass vial and the resulting suspension was stirred on magnetic plate. The suspension was then vacuum dried at room temperature to result in Form B.

Compound G (about 200 mg) also was reacted with maleic acid (about 20 mg; molar ratio of 1:0.5) using EtOAc as a solvent. The resulting suspension was stirred on a magnetic plate at about 600 rpm at room temperature. If white solid crashed out after stirring, about 9.0 mL of EtOAc was added to the suspension. The suspension was stirred for two days, and then isolated by centrifuge. The isolated solids were dried in the air or at 50° C. under vacuum overnight to result in Form A.

A summary of the compound G maleate salts made in the scale-up experiments can be found in Table 5.

TABLE 5

Scale-Up Experiments for Compound G Maleate Salt

| | Loading acid (compound G:acid) | MTBE | Acetone |
|---|---|---|---|
| 1 | Maleic acid (1:1) | Maleate Form A mixed with amorphous | Maleate Form B |
| 2 | Maleic acid(1:2) | Maleate Form A mixed with amorphous | Maleate Form B |

TABLE 5-continued

Scale-Up Experiments for Compound G Maleate Salt

| | Loading acid (compound G:acid) | EtOAc |
|---|---|---|
| 3 | Maleic acid (1:0.5) | Maleate Form A |
| 4 | Maleic acid (1:0.5) | Maleate Form A |
| 5 | Maleic acid (1:0.5) | Maleate Form A |

Figure 23:
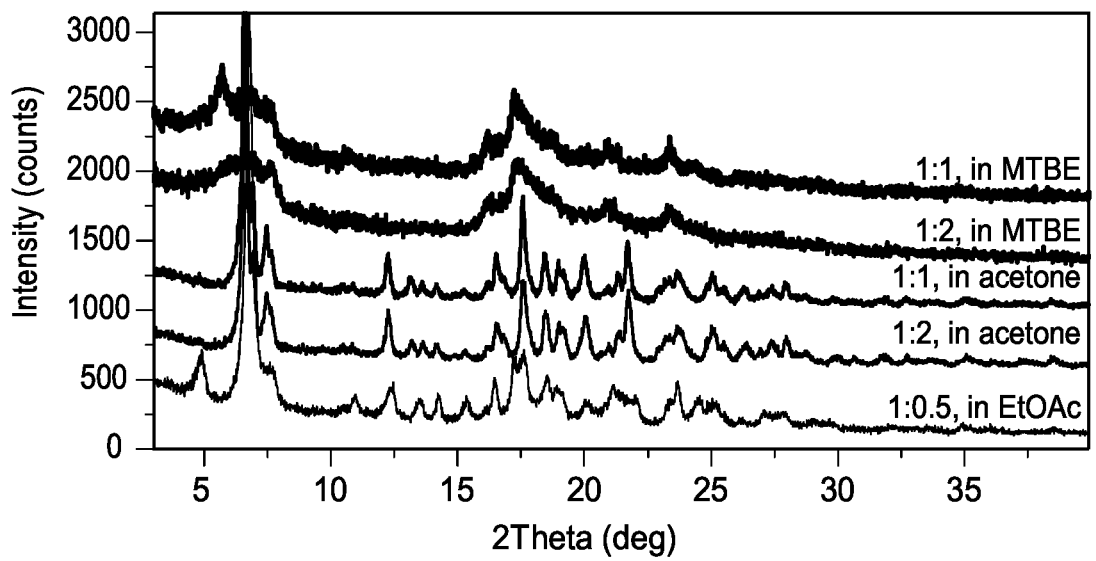
FIG. 23 depicts XRPD patterns of the monomaleate salt of compound G prepared in the indicated solvents (Forms A and B) using the indicated ratios of maleic acid, and vacuum dried at room temperature.
Figure 24:
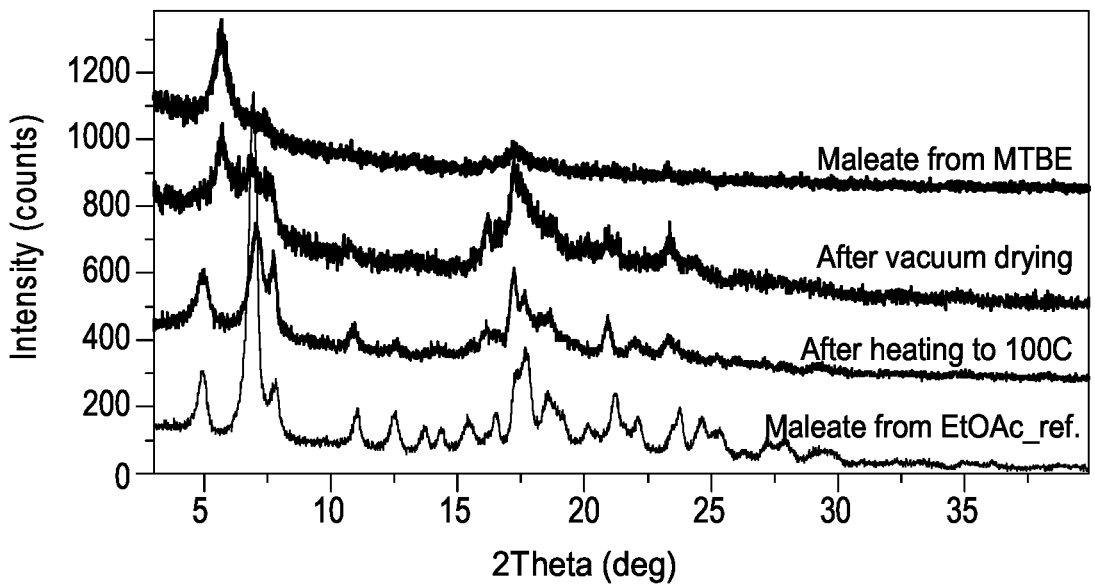
FIG. 24 depicts XRPD patterns of Form F (monomaleate salt of compound G prepared in MBTE) after vacuum drying and heating to 100° C. compared to Form A.
Figure 25:
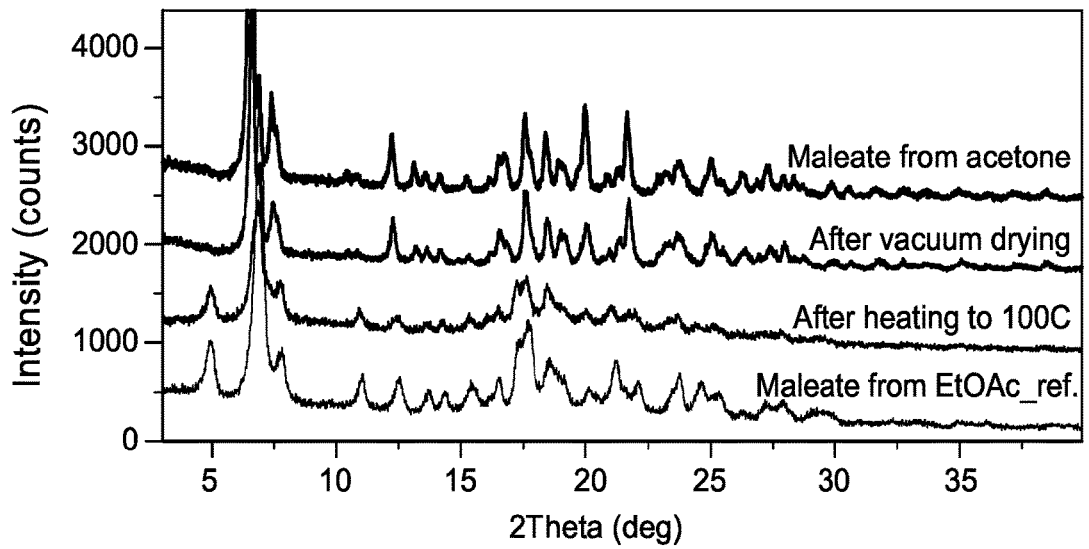
FIG. 25 depicts XRPD patterns of Form C (monomaleate salt of compound G prepared in acetone) after vacuum drying and heating to 100° C.

The XRPD results for the scale-up experiments are shown in FIG. 23. A consistent XRPD pattern was observed for maleate from the same solvent. The maleate from MTBE (Form A) showed weak crystallinity and the maleate from acetone (Form B) showed slightly different XRPD from that crystallized in EtOAc (Form A). However, after heat treatment to 100° C. by TGA, as shown in FIGS. 24 and 25, the XRPD of the monomaleate salt of compound G crystallized from MTBE (Form A) and acetone (Form B) matched well with that of the monomaleate salt crystallized from EtOAc (Form A).

Example 5: Further Processing and Characterization of Form A

Figure 26:
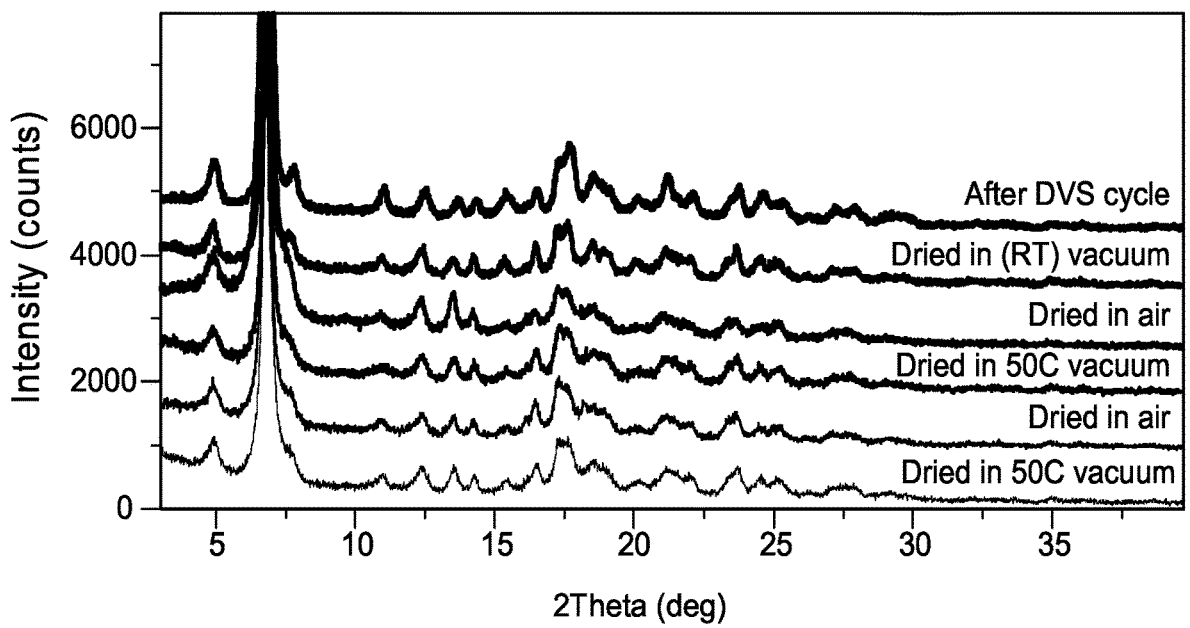
FIG. 26 depicts XRPD patterns of Form A (monomaleate salt of compound G prepared in EtOAc) after the indicated drying conditions.
Figure 27:
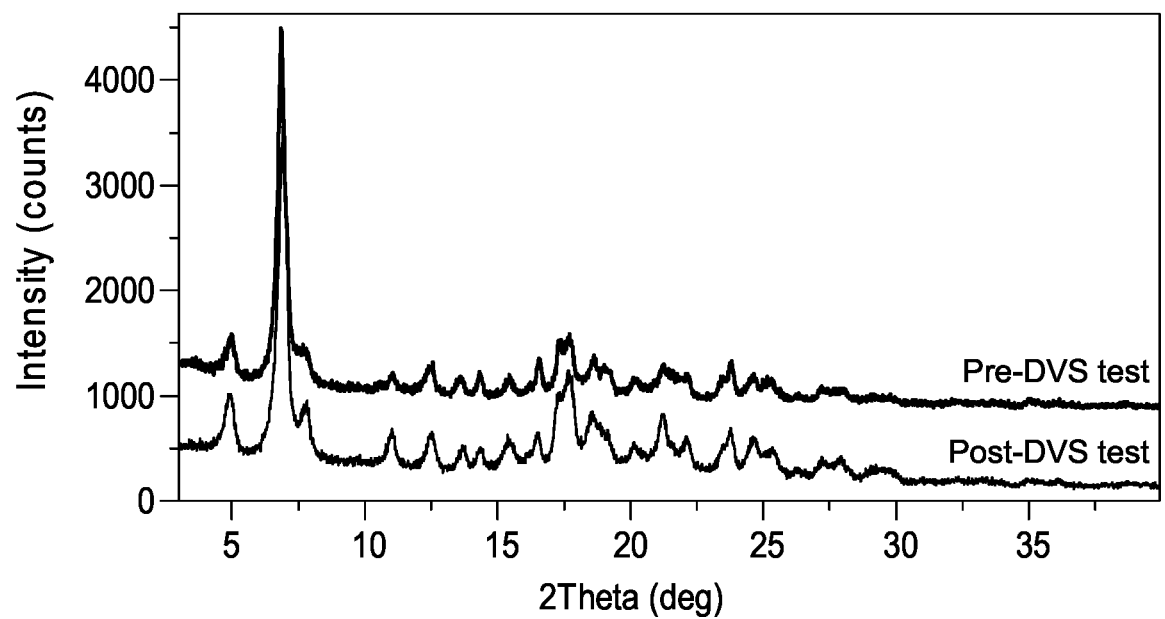
FIG. 27 depicts XRPD patterns of Form A (monomaleate salt of compound G prepared in EtOAc) before and after DVS testing.

Different drying conditions (air drying, vacuum drying, humidity cycle) were utilized to process Form A (crystallized from EtOAc). The resulting crystalline salts were characterized by XRPD (FIGS. 25 and 26), DSC, and TGA. Maleates after vacuum drying were also characterized by $^1$H NMR to determine the stoichiometry of freebase/maleic acid. The XRPD results in FIG. 26 show that all samples, under different drying conditions, possessed the same diffraction pattern. Dynamic vapor sorption testing (DVS) also was applied to characterize Form A from EtOAc, as shown in FIG. 4. Characterization data for these experiments is summarized in Table 6.

TABLE 6

Characterization Data of Form A (From EtOAc) at 1:0.5

| Drying condition | Weight loss in TGA (wt %) | Endotherm in DSC (° C.) | Stoichiometry from NMR (freeform/acid) |
|---|---|---|---|
| humidity cycle* | 1.8 | 138.8 | / |
| RT vacuum | 2.5 | 92.1, 140.7 | 1.0:1.0 |
| air | 2.5 | 145.1 | / |
| 50° C. vacuum | 0.4 | 147.6 | 1.0:1.0 |
| air | 2.3 | 144.5 | / |
| 50° C. vacuum | 2.1 | 145.5 | 1.0:1.1 |

*Humidity cycle (DVS) is 40% RH-95% RH-0% RH-95% RH-air conditions.

Example 6: Synthetic Procedures

Procedure 1: Preparation of the Monomaleate Salt of Compound G with Isopropyl Acetate/Ethanol To compound G (3.6 kg in 37.88 kg IPAc) was added EtOH (11.5 kg). The resulting solution was heated to 50° C. and maleic acid (1.62 kg of a 12.4 wt % solution in EtOH) was added in 15 min followed by a seed (18.0 g) of the desired compound. The suspension was stirred for 0.5 h at 50° C. and maleic acid (4.90 kg of a 13.4 wt % solution in EtOH) was added over 3 h. The mixture was stirred at 50° C. for 4 h, cooled to −3° C. over 9.5 h, held at −2-3° C. for 2 h, filtered, and washed with IPAc/EtOH (2:1, 12.0 kg) at −5-5° C. The wet cake was dried under vacuum at 40-45° C. for 17 h to provide the monomaleate salt of compound G (3.86 kg, 99.0% purity).

Procedure 2: Salt-Break to Generate Form A with Ethyl Acetate

To Form A (3.56 kg) was added IPAc (37.8 kg) at 15-25° C. followed by 3.5% NaHCO$_3$ (37.8 kg) and the resulting suspension was stirred for 1 h to provide a solution. The aqueous layer was removed and the organic layer was washed with 5% Na$_2$SO$_4$ (aqueous, 36.9 kg) at 15-25° C. The aqueous layer was removed and the organic layer was concentrated to 4-7 L below 45° C. Three times the organic layer was chased with ethyl acetate (32.0 kg) at 15-25° C. and the solution was concentrated to about 7-11 L below 45° C. Ethyl acetate (28.8 kg) was then added and the solution was heated to 45-55° C. Maleic acid (720 g) was dissolved in 19.4 kg of ethyl acetate and ¹⁄₁₀ of this solution was added over 30 min at 45-55° C. A seed (9.09 g) was added at 45-55° C. and the mixture was stirred for 30 min. The remainder of the maleic acid solution was added at 45-55° C. over 1 h. The mixture was stirred for an additional 2 h at 45-55° C. then cooled to 1° C. over 8 h. The mixture was stirred for 1 h at −5-5° C. then filtered, washed with ethyl acetate (13.0 kg), and dried at 40-50° C. under vacuum for 26-28 h to provide 3.42 kg of maleate salt (99.1% purity) as a colorless solid. The XRPD pattern is shown in FIG. 1, characteristic DSC data is shown in FIG. 2, TGA data is shown in FIG. 3.

Procedure 3: Preparation of the Monomaleate Salt of Compound G using 0.5 eq of Maleic Acid (Form A)

To compound G (100 mg, 0.170 mmol) in THF (0.5 mL) was added maleic acid (0.085 mmol, 9.9 mg in THF (0.5 mL). The mixture was allowed to stand overnight and filtered to provide the monomaleate salt of compound G (50.5 mg) as a colorless solid.

Procedure 4: Recrystallization of the Monomaleate Salt of Compound G

To Form A (0.05 g, 0.0852 mmol) was added ethanol (0.5 mL) and the solution was heated to reflux for 5 min and allowed to cool to 20° C. overnight. Purified compound was isolated as a colorless solid (42 mg).

A similar recrystallization method was carried out using the following solvents to provide the monomaleate salt of compound G: THF, iPrOH-EtOAc (1:1), iPrOH, iPrOH-toluene (1:1), dioxane, and acetonitrile.

Example 7: PK Study Using Form A

Form A was formulated for subcutaneous administration at a concentration of 45 mg/ml, as described in Table 7. The percent bioavailability (% F) of Form A when each formulation was administered as a single subcutaneous dose of about 3 mg/kg to cynomolgus monkeys (3 males/dose) also can be found in Table 7.

TABLE 7

Formulations Used for Monkey PK Study

| Formulation | pH | % F (monkey) |
|---|---|---|
| 10% polysorbate 80 (aq.) | 4.5 | 59.0 ± 10.1 |
| 10% KOLLIPHORE EL (aq.) | 4.5 | 62.3 ± 17.8 |
| 10% polysorbate 80/10% N-methyl-2-pyrrolidone (aq.) | 5 | 76.2 ± 7.8 |
| 10% KOLLIPHORE EL/10% N-methyl-2-pyrrolidone (aq.) | 5 | 68.3 ± 8.1 |
| water | 3.6 | 70.4 ± 15.1 |
| 1:1 (v/v) LABRASOL/propylene glycol | N/A | 45.2 ± 3.3 |

Example 8: Polymorph Screen

Method A: About 30 mg of compound G was added to the solvent indicated in Table 8, then shaken at 50° C. at a rate of 700 rpm. The residues of the compound were separated by centrifuge (5 min at 9,000 rpm) and investigated by XRPD, DSC, and TGA after 7 days, as shown in Table 8 and FIGS. 7-13.

Method B: To 50 mg of compound G was added methanol (1.0 mL), followed by MTBE (0.5 mL). After allowing the mixture to stand overnight, the precipitate was collected and investigated by XRPD, DSC, and TGA, as shown in Table 8 and FIGS. 19, and 20.

TABLE 8

Polymorph Screen

| Form | Method | Crystallization/ Slurry Solvent | XRPD (2θ ± 0.2°) | TGA | DSC |
|---|---|---|---|---|---|
| B | A | 3% H₂O/Acetone | 6.8, 7.2, 18.4, 6.6, 13.6, 22.0, 17.4, 14.5, 18.0, and 5.0 (FIG. 13) | | |
| C | A | Acetone | 6.6, 13.2, 7.4, 20.1, 13.6, 6.9, 16.9, 3.7, 17.9, and 19.9 (FIG. 7) | 6.0% weight loss was observed from 29.2 to 130.0° C. (FIG. 8) | Normalized: 67.2 J/g Onset: 141.9° C. Peak: 148.63° C. (FIG. 8) |
| D | A | Acetonitrile | 6.8, 4.9, 17.4, 15.3, 7.7, 3.4, 17.7, 13.6, 12.4, and 10.9 (FIG. 9) | 0.3% weight loss was observed from 26.8 to 130.0° C. (FIG. 10) | Normalized: 86.20 J/g Onset: 148.53° C. Peak: 151.75° C. (FIG. 10) |
| E | A | Isopropyl Alcohol | 6.5, 3.3, 7.3, 19.8, 6.8, 16.5, 12.1, 21.5, 4.0, and 13.0 (FIG. 11) | 0.9% weight loss was observed from 32.5 to 99.3° C. (FIG. 12) | Normalized: 57.8 J/g Onset: 138.2° C. Peak: 147.61° C. (FIG. 12) |
| F | B | MeOH/MTBE | 6.3, 7.1, 19.0, 17.5, 19.6, 17.9, 22.0, 13.5, 18.2, and 15.5 (FIG. 19) | 1.4% weight loss was observed from 31.9 to 99.4° C. (FIG. 20) | Normalized: 71.2 J/g Onset: 128.05° C. Peak: 135.46° C. (FIG. 20) |

Example 9: Further Processing and Characterization of Form B

Procedure: 2 g of compound G was added to 3% water in acetone (20 mL), then shaken at 50° C. at a rate of 700 rpm overnight. The residue was investigated by XRPD, DSC, and TGA.

The residue was dried under vacuum at room temperature or 30° C. for 1 h, 4 h, or 24 h. The XRPD results in FIGS. 14-15 show that all samples, under different drying conditions, possessed the same diffraction pattern. DSC/TGA results for the sample dried at room temperature overnight are shown in FIG. 16 and drying overnight at 30° C. is shown in FIG. 17. Dynamic vapor sorption testing (DVS) also were applied to characterize Form F from 3% H₂O/Acetone as shown in FIG. 18. After drying overnight at room temperature Karl Fisher test indicated that Form F had a water content of 2.51%.

Example 10: Characteristic Peaks for Forms A and C-G

Table 9, below, includes the XRPD peaks that are unique to each polymorph.

TABLE 9

Polymorph Screen

| Form | Unique XRPD Peaks (2θ ± 0.2°) | Height |
|---|---|---|
| A | 6.9 | 6261 |
| | 17.3 | 1237 |
| | 17.8 | 1030 |
| B | 7.2 | 7829 |
| | 18.4 | 4173 |
| | 22.0 | 1251 |

TABLE 9-continued

Polymorph Screen

| Form | Unique XRPD Peaks (2θ ± 0.2°) | Height |
|---|---|---|
| C | 7.4 | 2147 |
| | 13.2 | 2206 |
| | 20.1 | 1386 |
| D | 4.9 | 2818 |
| | 7.7 | 1637 |
| | 10.9 | 1033 |
| | 12.4 | 1259 |
| | 13.6 | 1445 |
| | 15.3 | 1975 |
| E | 6.4 | 17796 |
| | 7.3 | 1906 |
| | 19.8 | 1831 |
| F | 6.3 | 6553 |
| | 19.0 | 1690 |
| | 19.6 | 1155 |

Example 11: Stability of Form A

The stability of Form A and its freebase was tested at ambient conditions (25° C. and 4000 relative humidity, "RH"), and at elevated temperature and humidity (40° C. and 750% RH) over the duration of one month. The freebase form showed rapid decomposition at elevated temperature and humidity. However, no significant change in Form A was observed at the same conditions and over the same time period. See Table 10, below. Therefore, Form A exhibits increased stability over its freebase.

TABLE 10

Stability Comparison of Form A and its Freebase

| Form | Conditions | Lot # | % Purity at t = 0 | % Purity at 1 Month | % Decomposition |
|---|---|---|---|---|---|
| Freebase | 25° C./40% RH | 1 | 95.1 | 93.2 | 1.9 |
| | 25° C./40% RH | 2 | 85.6 | 84.0 | 1.6 |
| | 25° C./40% RH | 3 | 93.7 | 92.3 | 1.4 |
| | 40° C./75% RH | 1 | 95.1 | 92.3 | 67.5 |
| | 40° C./75% RH | 2 | 85.6 | 92.3 | 28.8 |
| | 40° C./75% RH | 3 | 93.7 | 72.5 | 21.1 |
| Maleate Salt | 25° C./40% RH | 4 | 99.1 | 99.1 | 0.0 |
| | 25° C./40% RH | 5 | 99.4 | 99.3 | 0.1 |
| | 40° C./75% RH | 4 | 99.1 | 98.9 | 0.2 |
| | 40° C./75% RH | 5 | 99.4 | 99.3 | 0.1 |

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

We claim:
1. A method of preparing a crystalline salt of compound G monomaleate, comprising admixing:
   (a) compound G:

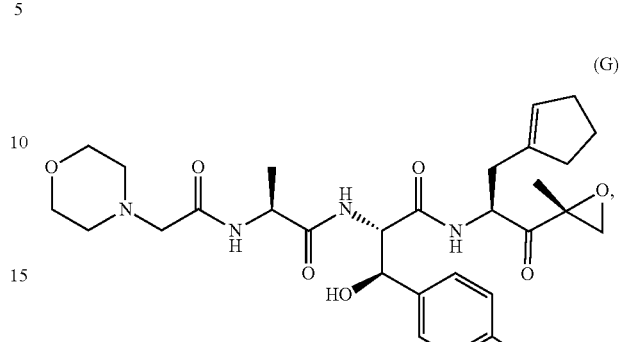

(b) maleic acid, and
   (c) a solvent
to form a suspension.

2. The method of claim 1, wherein the molar ratio of compound G to maleic acid is in a range of about 1:0.5 to 1:2.

3. The method of claim 2, wherein the molar ratio is 1:1.

4. The method of claim 1, wherein the solvent is selected from the group consisting of methanol ("MeOH"), ethanol ("EtOH"), isopropanol ("IPA"), ethyl acetate ("EtOAc"), isopropyl acetate ("IPAc"), tetrahydrofuran ("THF"), methyl tert-butyl ether ("MTBE"), acetone/n-heptane, acetone, diethyl ether ("Et$_2$O")/EtOAc, hexane/EtOAc, MTBE/EtOAc, toluene, 1,4-dioxane, acetonitrile ("ACN"), 1-butanol, aqueous mixtures of the foregoing, and combinations thereof.

5. The method of claim 4, wherein the solvent comprises EtOAc, IPAc, EtOH, aqueous mixtures thereof, or combinations thereof.

6. The method of claim 1, wherein the admixing occurs at a temperature in a range of 0° C. to 80° C.

7. The method of claim 6, wherein the admixing occurs at a temperature in a range of 40° C. to 60° C.

8. The method of claim 1, further comprising cooling the suspension to 0° C.

9. The method of claim 8, further comprising filtering the suspension to form a cake.

10. The method of claim 9, further comprising washing, drying, or both washing and drying the cake.

11. The method of claim 10, further comprising recrystallizing the cake.

12. The method of claim 10, further comprising
   (i) reforming compound G from the cake; and
   (ii) admixing the reformed compound G, maleic acid, and a solvent to form the crystalline salt.

13. The method of claim 11, wherein the crystalline salt has an X-ray powder diffraction ("XRPD") comprising peaks at 6.9, 17.3, and 17.8±0.2° 2θ using Cu Kα radiation ("Form A").

14. The method of claim 11, wherein the crystalline salt has an X-ray powder diffraction ("XRPD") comprising peaks at 7.2, 18.4, and 22.0±0.2° 2θ using Cu Kα radiation ("Form B").

15. The method of claim 11, wherein the crystalline salt has an X-ray powder diffraction ("XRPD") comprising peaks at 7.4, 13.2, and 20.1±0.2° 2θ using Cu Kα radiation ("Form C").

16. The method of claim 11, wherein the crystalline salt has an X-ray powder diffraction ("XRPD") comprising peaks at 4.9, 7.7, 10.9, 12.4, 13.6, and 15.3±0.2° 2θ using Cu Kα radiation ("Form D").

17. The method of claim 11, wherein the crystalline salt has an X-ray powder diffraction ("XRPD") comprising peaks at 6.4, 7.3, and 19.8±0.2° 2θ using Cu Kα radiation ("Form E").

18. The method of claim 11, wherein the crystalline salt has an X-ray powder diffraction ("XRPD") comprising peaks at 6.3, 19.0, and 19.6±0.2° 2θ using Cu Kα radiation ("Form F").

\* \* \* \* \*

UNITED STATES PATENT AND TRADEMARK OFFICE
CERTIFICATE OF CORRECTION

| | | |
|---|---|---|
| PATENT NO. | : 11,891,383 B2 | Page 1 of 1 |
| APPLICATION NO. | : 17/953935 | |
| DATED | : February 6, 2024 | |
| INVENTOR(S) | : Henry Johnson et al. | |

It is certified that error appears in the above-identified patent and that said Letters Patent is hereby corrected as shown below:

In the Claims

At Column 39, Line 3, "20" should be --2θ--.

Signed and Sealed this
Third Day of September, 2024

Katherine Kelly Vidal
*Director of the United States Patent and Trademark Office*